US011191653B2

United States Patent
Grandmaison et al.

(10) Patent No.: US 11,191,653 B2
(45) Date of Patent: Dec. 7, 2021

(54) POWERED LOWER LIMB DEVICES AND METHODS OF CONTROL THEREOF

(71) Applicant: UNIVERSITY OF NEW BRUNSWICK, Fredericton (CA)

(72) Inventors: Christian Grandmaison, Edmundston (CA); Jonathon Sensinger, Fredericton (CA)

(73) Assignee: UNIVERSITY OF NEW BRUNSWICK, Fredericton (CA)

( * ) Notice: Subject to any disclaimer, the term of this patent is extended or adjusted under 35 U.S.C. 154(b) by 558 days.

(21) Appl. No.: 15/803,176

(22) Filed: Nov. 3, 2017

(65) Prior Publication Data

US 2018/0116828 A1    May 3, 2018

Related U.S. Application Data

(60) Provisional application No. 62/417,192, filed on Nov. 3, 2016.

(51) Int. Cl.
*A61H 3/00* (2006.01)
*A61H 1/02* (2006.01)
(Continued)

(52) U.S. Cl.
CPC ............ *A61F 2/70* (2013.01); *A61F 5/0123* (2013.01); *A61H 1/024* (2013.01); *A61H 3/00* (2013.01);
(Continued)

(58) Field of Classification Search
CPC ........... B25J 9/0006; B25J 9/106; A61H 1/00; A61H 1/0218; A61H 1/0262;
(Continued)

(56) References Cited

U.S. PATENT DOCUMENTS 7,190,141 B1   3/2007 Ashrafiuon et al.
7,628,766 B1 * 12/2009 Kazerooni ............... A61F 5/00
602/16
(Continued)

FOREIGN PATENT DOCUMENTS

WO   WO-2004043307 A1 *  5/2004 ............. A61H 1/024
WO   WO-2016034755 A1 *  3/2016 ............... A61F 5/01
(Continued)

OTHER PUBLICATIONS

Cenciarini, M. et al., "Biomechanical Considerations in the Design of Lower Limb Exoskeletons", 2011 IEEE Int Conf. on Rehab. Rob. (2011).

(Continued)

*Primary Examiner* — Quang D Thanh
(74) *Attorney, Agent, or Firm* — Hill & Schumacher

(57) ABSTRACT

Methods are provided for controlling a powered lower limb device. A stance phase control method is disclosed in which the required joint torque is determined based on the difference between two joint angles, such as the knee joint and the ankle joint. A swing control method is also disclosed that employs feedback-based minimum jerk trajectory control. A joint assembly for use in a modular lower limb device is also provided. The joint assembly includes a reconfigurable slider-crank mechanism that is configurable to provide a plurality of different ranges of rotational travel, rotational speeds, and torques, for customization according to different anatomical joints. The joint assembly may include a compact coupling device for coupling a ball screw of the slider-crank mechanism to an output shaft of a motor. When employed to form a modular orthosis, the joint assembly may be adapted for self-alignment as its length adjustment method during setup.

28 Claims, 19 Drawing Sheets

(51) Int. Cl.
| | |
|---|---|
| A61F 5/01 | (2006.01) |
| A61F 2/68 | (2006.01) |
| A61F 2/70 | (2006.01) |
| B25J 9/00 | (2006.01) |
| B25J 9/10 | (2006.01) |
| A61F 2/76 | (2006.01) |

(52) U.S. Cl.
CPC .............. *B25J 9/0006* (2013.01); *B25J 9/106* (2013.01); *A61F 2002/7625* (2013.01); *A61H 2003/007* (2013.01); *A61H 2201/1207* (2013.01); *A61H 2201/1409* (2013.01); *A61H 2201/1418* (2013.01); *A61H 2201/1436* (2013.01); *A61H 2201/5007* (2013.01); *A61H 2201/5061* (2013.01); *A61H 2201/5069* (2013.01); *A61H 2205/10* (2013.01)

(58) Field of Classification Search
CPC ...... A61H 2201/165; A61H 2201/5061; A61H 2201/5064; A61H 2201/5069; A61H 3/00; A61H 2201/1215; A61H 2201/5007; A61H 2201/1628; A61H 2201/163; A61H 1/024; A61H 2201/1436; A61H 2003/007; A61H 2205/10; A61H 2201/1418; A61H 2201/1409; A61H 2201/1207; A61F 5/0123; A61F 2005/0132; A61F 2005/0137; A61F 2005/0141; A61F 2005/0165; A61F 2005/0167; A61F 2/68; A61F 2002/7625; A61F 2/70; Y10T 403/32073

See application file for complete search history.

(56) References Cited

U.S. PATENT DOCUMENTS

| | | | |
|---|---|---|---|
| 8,366,591 | B2 | 2/2013 | Patoglu |
| 9,044,859 | B2 | 6/2015 | Cory |
| 10,213,324 | B2 | 2/2019 | Lenzi et al. |
| 10,278,885 | B1* | 5/2019 | Smith .................. A61H 1/0237 |
| 10,314,723 | B2 | 6/2019 | Gregg et al. |
| 2009/0299244 | A1* | 12/2009 | Chiang ................. A61F 5/0123 602/26 |
| 2014/0364962 | A1 | 12/2014 | Gregg et al. |
| 2015/0025423 | A1* | 1/2015 | Caires .................... A61H 1/024 601/35 |
| 2015/0173929 | A1* | 6/2015 | Kazerooni ............... A61H 3/00 602/16 |
| 2015/0190248 | A1 | 7/2015 | Vitiello et al. |
| 2015/0351995 | A1* | 12/2015 | Zoss ..................... A61H 1/024 623/32 |
| 2016/0058582 | A1 | 3/2016 | Lenzi et al. |
| 2016/0074180 | A1 | 3/2016 | Lenzi et al. |
| 2016/0158029 | A1 | 6/2016 | Kuiken et al. |
| 2017/0340504 | A1* | 11/2017 | Sanz Merodio ......... A61H 3/00 |

FOREIGN PATENT DOCUMENTS

| | | |
|---|---|---|
| WO | 2016130745 A1 | 8/2016 |
| WO | 2016146960 A1 | 9/2016 |

OTHER PUBLICATIONS

Wang, S. et al., "Design and Control of the MINDWALKER Exoskeleton", IEEE Trans. Neural Sys. and Rehab. Eng. 23, 277-286 (2015).

Griffin, B. et al., "Nonholonomic Virtual Constraints for Dynamic Walking", 2015 54th IEEE Conf. on Dec. and Con. (CDC) (2015).

Bartenbach, V. et al., "A Lower Limb Exoskeleton Research Platform to Investigate Human-Robot Interaction", 2015 IEEE Int. Conf. on Rehab. Rob (ICORR) (2015).

Bartenbach, V. et al., "Concept and Design of a Modular Lower Limb Exoskeleton", 6th IEEE RAS/EMBS Int. Conf. on Biomed Rob. and Biomech. (BioRob) (2016).

Chen, B. et al., "Recent developments and challenges of lower extremity exoskeletons", J. Ortho. Trans. 5, 26-37 (2016).

M. Vukobratovic and D. Juricic, "Contribution to the Sythesis of Biped Gait," IEEE Trans. Biomed. Eng., BME-16, No. 1, pp. 1-6, 1969.

M. Vukobratovic, D. Hristic, and Z. Stojiljkovic, "Development of active anthropomorphic exoskeletons," Med. Biol. Eng., vol. 12, No. 1, pp. 66-80, 1974.

C. Ray and J. West, "Social, sexual and personal implications of paraplegia," Paraplegia, vol. 22, No. 2. pp. 75-86, 1984.

T. Flash and N. Hogan, "The coordination of arm movements: an experimentally confirmed mathematical model.," J. Neurosci., vol. 5, No. 7, pp. 1688-1703, 1985.

Bortole, M. (2013), "Master Thesis: Design and Control of a Robotic Exoskeleton for Gait Rehabilitation," 95 pages, (Sep. 2013).

Villarreal, D., Poonawalla, H.A., and Gregg, R., "A Robust Parameterization of Human Gait Patterns Across Phase-Shifting Perturbations," IEEE Transactions on Neural Systems and Rehabilitation Engineering, vol. 25, No. 3, pp. 1-14, Mar. 2017.

C. Chevallereau, G. Abba, Y. Aoustin, F. Plestan, E. R. Westervelt, C. Canudas-De-Wit, and J. W. Grizzle, "RABBIT: A testbed for advanced control theory," IEEE Control Syst. Mag., paper No. CSM-02-038, vol. 23, No. 5, pp. 1-51, 2003.

S. Jezernik, G. Colombo, T. Keller, H. Frueh, and M. Morari, "Robotic Orthosis Lokomat: A Rehabilitation and Research Tool," Neuromodulation, vol. 6, No. 2, pp. 108-115, 2003.

K. Loffler, M. Gienger, and F. Pfeiffer, "Sensor and control design of a dynamically stable biped robot," 2003 IEEE Int. Conf. Robot. Autom. (Cat. No. 03CH37422), vol. 1, pp. 484-490, Sep. 14-19, 2003.

Villarreal, D. and Gregg, R., "A Survey of Phase Variable Candidates of Human Locomotion," Conf Proc IEEE Eng Med Biol Soc., Author manuscript; available in PMC, Jan. 9, 2015, 15 pages.

A. B. Zoss, H. Kazerooni, and A. Chu, "Biomechanical Design of the Berkeley Lower Extremity Exoskeleton (BLEEX)," IEEE/ASME Trans. Mechatronics, vol. 11, No. 2, pp. 128-138, 2006.

D. Liu and E. Todorov, "Evidence for the flexible sensorimotor strategies predicted by optimal feedback control.," J. Neurosci., vol. 27, No. 35, pp. 9354-9368, 2007.

E. R. Westervelt, J. W. Grizzle, C. Chevallereau, J. H. Choi, and B. Morris, "Feedback Control of Dynamic Bipedal Robot Locomotion," 521 pages, 2007.

A. M. Dollar and H. Herr, "Lower Extremity Exoskeletons and Active Orthoses: Challenges and State-of-the-Art," IEEE Trans. Robot., vol. 24, No. 1, pp. 144-158, 2008.

Kanehiro, F., Morisawa, M., Suleiman, W., Kaneko, K., and Yoshida, E., "Reactive Leg Motion Generation Method Under Consideration of Physical Constraints," JRSJ, vol. 28, No. 10, pp. 1251-1261, 2010, with English Abstract.

H. K. Kwa, J. H. Noorden, M. Missel, T. Craig, J. E. Pratt, and P. D. Neuhaus, "Development of the IHMC mobility assist exoskeleton," Proc.—IEEE Int. Conf. Robot. Autom., pp. 2556-2562, 2009.

C. Chevallereau, J. W. Grizzle, and C. Shih, "Asymptotically Stable Walking of a Five-Link Underactuated 3D Bipedal Robot," vol. 25, No. 1, pp. 37-50, 2010.

E. Swinnen, S. Duerinck, J.-P. Baeyens, R. Meeusen, and E. Kerckhofs, "Effectiveness of robot-assisted gait training in persons with spinal cord injury: a systematic review.," J. Rehabil. Med., vol. 42, No. 6, pp. 520-526, 2010.

R. J. Farris, H. A. Quintero, and M. Goldfarb, "Preliminary evaluation of a powered lower limb orthosis to aid walking in paraplegic individuals," IEEE Trans. Neural Syst. Rehabil. Eng., vol. 19, No. 6, pp. 652-659, 2011.

B. E. Lawson, H. A. Varol, and M. Goldfarb, "Ground adaptive standing controller for a powered transfemoral prosthesis," IEEE Int. Conf. Rehabil. Robot., 6 pages, 2011.

(56) References Cited

OTHER PUBLICATIONS

P. D. Neuhaus, J. H. Noorden, T. J. Craig, T. Torres, J. Kirschbaum, and J. E. Pratt, "Design and evaluation of Mina: A robotic orthosis for paraplegics," 2011 IEEE Int. Conf. Rehabil. Robot., pp. 1-8, 2011.
H. A. Quintero, R. J. Farris, C. Hartigan, I. Clesson, and M. Goldfarb, "A Powered Lower Limb Orthosis for Providing Legged Mobility in Paraplegic Individuals.," Top. Spinal Cord Inj. Rehabil., vol. 17, No. 1, pp. 25-33, 2011.
K. A. Strausser and H. Kazerooni, "The development and testing of a human machine interface for a mobile medical exoskeleton," 2011 IEEE/RSJ Int. Conf. Intell. Robot. Syst., pp. 4911-4916, 2011.
Lenzi et al., Design and Preliminary Testing of the RIC Hybrid Knee Prosthesis, IEEE Engineering in Medicine and Biology Society (EMBC) conference, Aug. 25-29, 2015, pp. 1683-1686.
Farris, R. J. (2012), "Design of a powered lower-limb exoskeleton and control for gait assistance in paraplegics," p. 1-114, 2012.
R. J. Farris, H. A. Quintero, and M. Goldfarb, "Performance evaluation of a lower limb exoskeleton for stair ascent and descent with Paraplegia," Proc. Annu. Int. Conf. IEEE Eng. Med. Biol. Soc. EMBS, pp. 1908-1911, 2012.
Winter, D., "Biomechanics and Motor Control of Human Movement," 1990, pp. 213; 250-260; 266-267.
Winter, D., "The Biomechanics and Motor Control of Human Gait: Normal, Elderly and Pathological", 1991. pp. 121-132.
T. Yan, M. Cempini, C. M. Oddo, and N. Vitiello, "Review of assistive strategies in powered lower-limb orthoses and exoskeletons," Rob. Auton. Syst., vol. 64, pp. 120-136, 2015.
H. W. Park, A. Ramezani, and J. W. Grizzle, "A finite-state machine for accommodating unexpected large ground-height variations in bipedal Robot Walking," IEEE Trans. Robot., vol. 29, No. 2, pp. 331-345, 2013.
S. Wang, L. Wang, C. Meijneke, E. Van Asseldonk, T. Hoellinger, G. Cheron, Y. Ivanenko, V. La Scaleia, F. Sylos-Labini, M. Molinari, F. Tamburella, I. Pisotta, F. Thorsteinsson, M. Ilzkovitz, J. Gancet, Y. Nevatia, R. Hauffe, F. Zanow, and H. Van Der Kooij, "Design and Control of the Mindwalker Exoskeleton," IEEE Trans. Neural Syst. Rehabil. Eng., vol. 23, No. 2, pp. 277-286, 2014.
T. Lenzi, L. Hargrove, and J. W. Sensinger, "Speed-Adaptation Mechanism: Robotic Prostheses Can Actively Regulate Joint Torque," Robotics, vol. 21, No. 4, pp. 94-107, 2014.
R. D. Gregg, T. Lenzi, L. J. Hargrove, and J. W. Sensinger, "Virtual Constraint Control of a Powered Prosthetic Leg: From Simulation to Experiments With Transfemoral Amputees," IEEE Trans. Robot., vol. 30, No. 6, pp. 1455-1471, 2014.

\* cited by examiner

POWERED LOWER LIMB DEVICES AND METHODS OF CONTROL THEREOF

CROSS-REFERENCE TO RELATED APPLICATION

This application claims priority to U.S. Provisional Application No. 62/417,192, titled "POWERED LOWER LIMB DEVICES AND METHODS OF CONTROL THEREOF" and filed on Nov. 3, 2016, the entire contents of which is incorporated herein by reference.

BACKGROUND

The present disclosure relates to powered prosthetic and orthotic devices, and to bipedal robotic devices.

Every year, more than 7800 people incur a spinal cord injury in North America. Although around 44% will end up with complete loss of locomotion, the fortunate ones can benefit from clinical rehabilitation to help recover motor control. Some therapy methods make use of a powered exoskeleton to support the impaired limbs, and guide them through the human walking cycle numerous times. Powered orthoses, such as powered exoskeletons, offer the promise of low-cost rehabilitation, together with empowering wheelchair bound individuals to walk, climb stairs, and stand again. Current commercially available exoskeletons fail to accurately replicate the human walk due to their non-powered ankle design or inadequate control scheme.

In order to fully realize their potential, improvements in such devices are needed to allow for truly natural gait and reduced energy cost for the user. These improvements largely fall into two categories: actuator design, and control system design. Advances in electric motor power density are allowing for more robust and powerful actuator designs to be realized. Additionally, natural gait has been achieved in powered prostheses using various forms of autonomous control. Similarly, autonomous virtual constraint control in bipedal robotics has allowed for robust control with guaranteed stability. Autonomous gait controllers, such as virtual constraint control, have yet to be applied to a hip-knee-ankle-foot system, such as a powered orthosis.

Current control systems of powered rehabilitation orthoses are typically high performance in the sense of natural gait replication, or highly safe in the sense of user stability. However, due to their control structures, they often fail to achieve both goals.

SUMMARY

In some aspects, methods are provided for controlling a powered lower limb device. A stance phase control method is disclosed in which the required joint torque is determined based on the difference between two joint angles, such as the knee joint and the ankle joint. In other embodiments, a joint assembly for use in modular lower limb devices is provided. The joint assembly includes a reconfigurable slider-crank mechanism that is configurable to provide a plurality of different ranges of rotational travel, rotational speeds, and torques, for customization according to different anatomical joints. The joint assembly may include a compact coupling device for coupling a ball screw of the slider-crank mechanism to an output shaft of a motor. When employed to form a modular orthosis, the joint assembly may be adapted for self-alignment as its length adjustment method during setup.

Accordingly, in a first aspect, there is provided a method of controlling a hip joint of a lower limb device during a subphase of a stance phase, the lower limb device further comprising a knee joint and an ankle joint, the method comprising:
  receiving angle sensor information from angle sensors respectively associated with the knee joint and the ankle joint;
  receiving inertial sensor information from one or more inertial sensors associated with the lower limb device;
  processing the angle sensor information to determine a knee joint angle and an ankle joint angle;
  determining a phase variable dependent on a difference between the knee joint angle and the ankle joint angle;
  processing the inertial sensor information to determine a walking speed of the lower limb device; and
  controlling a hip joint actuator such that a hip joint torque applied to the hip joint is constrained according to a pre-determined dependence on the phase variable and the walking speed.

In another aspect, there is provided a method of controlling a lower limb device during a subphase of a stance phase, the lower limb device comprising a hip joint, a knee joint and an ankle joint, the method comprising:
  receiving angle sensor information from angle sensors respectively associated with the knee joint and the ankle joint;
  receiving inertial sensor information from one or more inertial sensors associated with the lower limb device;
  processing the angle sensor information to determine a knee joint angle and an ankle joint angle;
  determining a phase variable dependent on a difference between the knee joint angle and the ankle joint angle;
  processing the inertial sensor information to determine a walking speed of the lower limb device;
  controlling a hip torque applied by a hip joint actuator to the hip joint according to a first pre-determined dependence of hip torque on the phase variable and the walking speed;
  controlling a knee joint actuator such that a knee joint torque applied to the knee joint satisfies a second pre-determined dependence of the knee joint torque on the phase variable and the walking speed; and
  controlling an ankle joint actuator such that an ankle joint torque applied to the ankle joint satisfies a third pre-determined dependence of the ankle joint torque on the phase variable and the walking speed;
  such that the hip joint actuator, the knee joint actuator and the ankle joint actuator are all controlled according to the same phase variable.

In another aspect, there is provided a method of controlling a selected joint of a lower limb device during a subphase of a stance phase, the lower limb device comprising a plurality of joints, the method comprising:
  receiving angle sensor information from angle sensors respectively associated with two joints of the plurality of joints;
  receiving inertial sensor information from one or more inertia sensors associated with the lower limb device;
  processing the angle sensor information in order to determine a phase variable dependent on joint angles of the two joints;
  processing the inertial sensor information to determine a walking speed of the lower limb device; and
  controlling an actuator associated with the selected joint such that a joint torque applied to the selected joint satisfies a pre-determined dependence of the joint torque on the phase variable and the walking speed.

In another aspect, there is provided a method of controlling a hip joint of an orthosis during a subphase of a stance phase, the method comprising:
- receiving angle sensor information from angle sensors respectively associated with a knee joint and an ankle joint of a wearer of the orthosis;
- receiving inertial sensor information from one or more inertia sensors associated with the orthosis;
- processing the angle sensor information to determine a knee joint angle and an ankle joint angle associated with the wearer of the orthosis;
- determining a phase variable dependent on a difference between the knee joint angle and the ankle joint angle;
- processing the inertial sensor information to determine a walking speed of the orthosis; and
- controlling a hip joint actuator such that a hip joint torque applied to the hip joint satisfies a pre-determined dependence of the hip joint torque on the phase variable and the walking speed.

In another aspect, there is provided a joint assembly for use with a modular powered prosthesis or a modular powered orthosis, the joint assembly comprising:
- a support frame;
- a motor supported by said support frame;
- a screw coupled to an output shaft associated with said motor, said screw comprising a nut;
- a crank pivotally connected to said support frame, thereby forming a joint;
- a coupling link for mechanically coupling said nut to said crank, such that linear actuation of said nut by said motor responsively produces rotation of said crank about the joint;
- wherein a distal portion of said coupling link is connectable to said crank at a plurality of selectable anchor points; and
- wherein each selectable anchor point is configured to provide a respective range of rotational travel, rotational speed, and torque that is customized for a respective anatomical joint.

In another aspect, there is provided a coupling assembly configured to connect an output shaft associated with a motor to a secondary shaft, the coupling assembly comprising:
- a coupling for securing the secondary shaft to the output shaft; and
- a coupling housing connectable to a non-rotating portion of the motor;
- wherein said coupling is rotatably supported within said coupling housing by a first angular contact bearing and a second angular contact bearing; and
- wherein said first angular contact bearing and said second angular contact bearing are arranged in a back-to-back configuration and reside between an inner surface of said coupling housing and an outer surface of said coupling A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
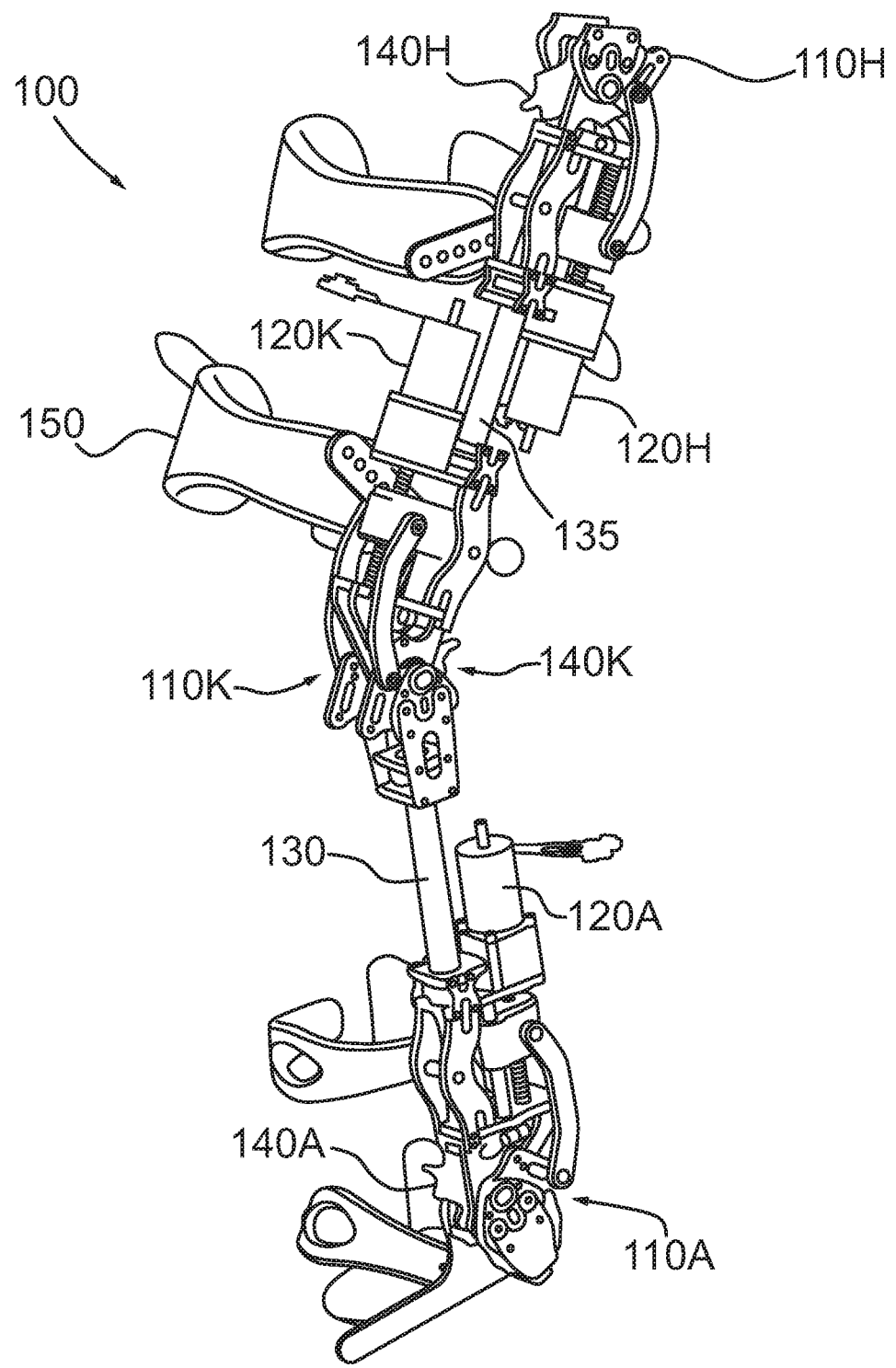
FIG. 1A shows an example of a lower limb device.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "virtual constraint" refers to a rule or constraint applied or enforced by a control system to cause an orthotic (e.g. exoskeleton), prosthetic or robotic device to adjust its joint elements, such as position, velocity, or torque, in response to the value of a monotonic phase variable.

As used herein, the phrase "holonomic virtual constraint" refers to a kinematic relationship between links of a device that is enforced via feedback, where a single phase variable is employed per constraint.

As used herein, the phrase "function" or "function relationship" refers to a relation between a set of inputs and a set of permissible outputs with the property that each input is related to exactly one output.

Figure 15:
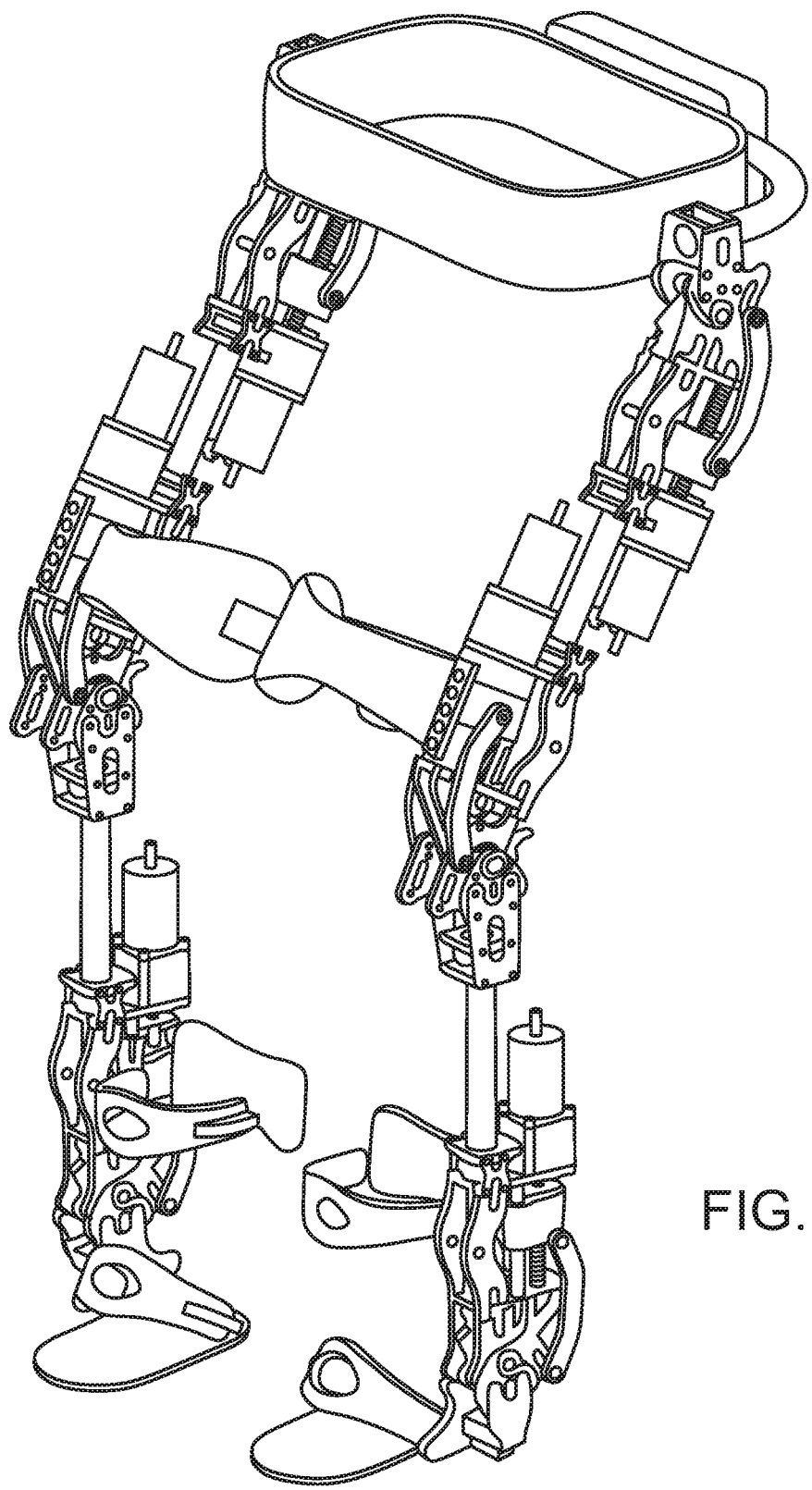
FIG. 15 shows an example isometric view of a modular exoskeleton system, including an attachment to the hip actuators.

Referring now to FIG. 1A, an example of a lower limb orthosis is shown. The example lower limb orthosis 100 includes three powered joints—a powered ankle joint 110A, a powered knee joint 110K, and a powered hip joint 110H, each actuated by respective motors 120A, 120K and 120H. The device attaches on the outside of the operator's lower limbs via adjustable cuffs 150, and is linked together around the back of the user's waist by a support brace (not shown in the figure, but shown in FIG. 15).

The powered knee joint 110K is connected to the powered hip joint 110H and the powered ankle joint by respective connection rods 130 and 135. The joint angles of the ankle joint, the knee joint and the hip joint are measurable based on signals received from respective angle sensors 140A, 140K and 140H. One or more inertial sensors (not shown in FIG. 1A) may be employed to generate signals that can be processed to determine kinematic measures such as velocity and acceleration. One or more additional sensors may be employed to provide signals that can be processed in order to determine the instantaneous gait phase (stance or swing) during use of the lower limb device, as well as to detect subphases of the stance phase.

Figure 1B:
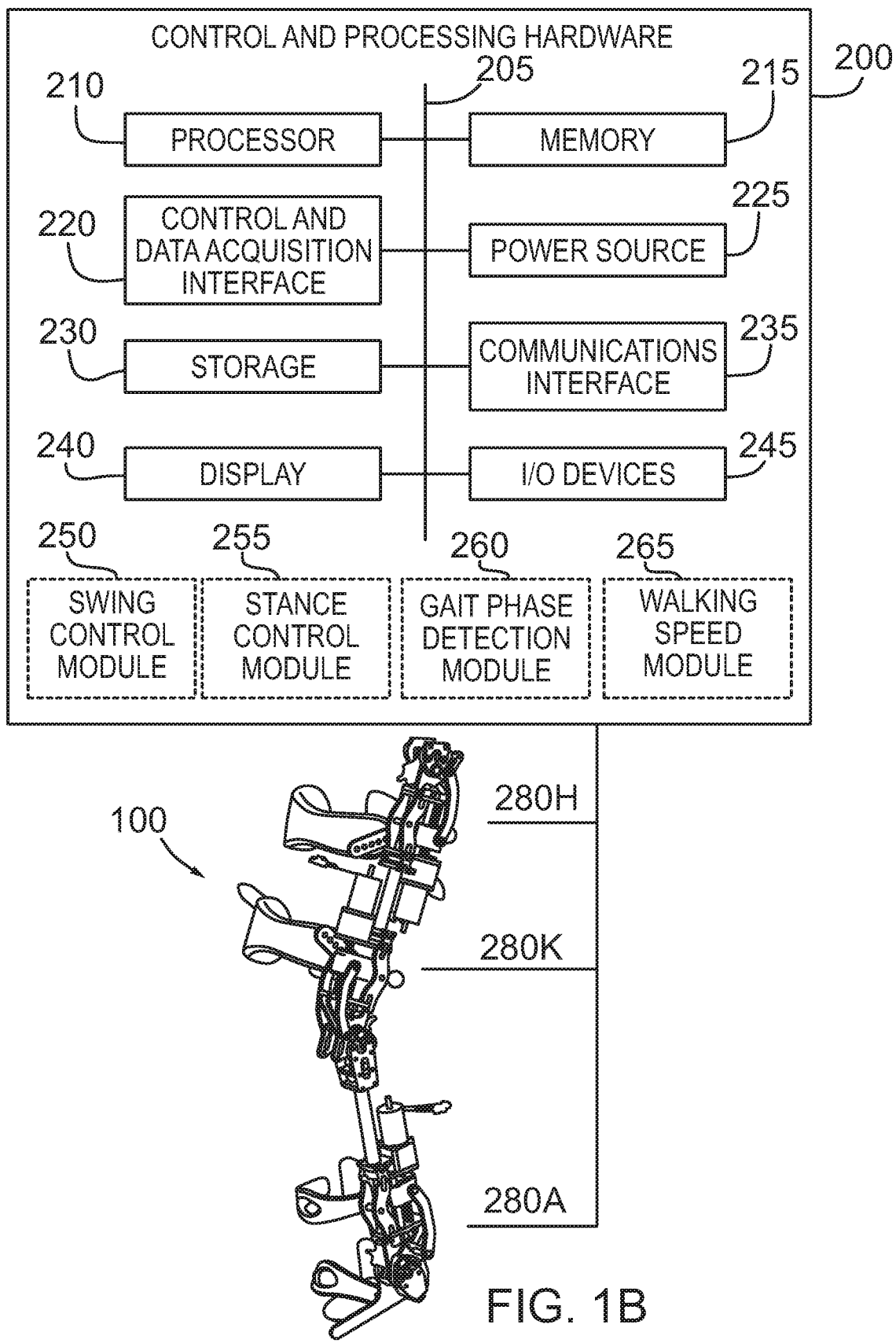
FIG. 1B shows an example system including a lower limb device and a controller.

Referring now to FIG. 1B, an example powered lower limb system is shown that includes a powered lower limb device 100 that is operatively coupled to a control and processing unit 200. The figure schematically illustrates the connection of the control and processing hardware 200 to various joint actuators and sensors of the lower limb device 100, including connections to a hip actuator and hip angle sensors 280H, a knee actuator and knee angle sensors 280K, and an ankle actuator and ankle angle sensors 280A (although not shown in the figure, the control and processing hardware is also connected to one or more inertial sensors associated with the lower limb device 100, and to one or more additional sensors for gait phase determination). Although the lower limb device 100 is shown as powered orthosis having powered hip, knee and ankle actuators, it will be understood that this orthosis is merely provided as an example, and that the control and processing system 200 may be employed to control a wide variety of powered devices for gait control, such as orthoses (e.g. exoskeletons), prostheses, and robotic devices.

As shown in the example embodiment illustrated in FIG. 1B, control and processing hardware 200 may include a processor 210, a memory 215, a system bus 205, a data acquisition and control interface 220 for acquiring sensor data and for sending control commands to the lower limb device 100, a power source 225, and a plurality of optional additional devices or components such as storage device 230, communications interface 235, display 240, and one or more input/output devices 245.

The example methods described herebelow for controlling a powered lower limb device can be implemented via processor 210 and/or memory 215. As shown in FIG. 1B, the processing of sensor signals in order to provide gait control the powered lower limb device 100 is performed by control and processing hardware 200, via executable instructions represented as swing control module 250, stance control module 255, and gait phase (and subphase) detection module 260, and a walking speed detection module 265. Various examples of these control algorithms are described in detail below.

It is to be understood that the example system shown in the figure is not intended to be limited to the components that may be employed in a given implementation. For example, in one example implementation, the processing hardware 200 may be provided on a computing device that is supported by the lower limb device 100. Alternatively, one or more components of the processing hardware 200 may be physically separate from the lower limb device 100. For example, the processing and computing hardware 200 may include a mobile computing device, such as a tablet or smartphone that is connected to a local processing hardware supported by the lower limb device via one or more wired or wireless connections. In another example implementation, a portion of the control and processing hardware 200 may be implemented, at least in part, on a remote computing system that connects to a local processing hardware via a remote network, such that some aspects of the processing are performed remotely (e.g. in the cloud).

The methods described herein can be partially implemented via hardware logic in processor 210 and partially using the instructions stored in memory 215. Some embodiments may be implemented using processor 210 without additional instructions stored in memory 215. Some embodiments are implemented using the instructions stored in memory 215 for execution by one or more microprocessors. A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

As indicated in FIG. 1B, the lower limb device may be controlled according to the phase of the gait cycle, where separate control algorithms are employed during the swing phase and the stance phase. As shown at 260, a gait phase detection module may be employed to process signals from sensors associated with the lower limb device 100 in order to determine a gait phase thereof. Depending on the type of swing and stance phase control algorithms employed, the signals may also be processed to determine a subphase (e.g. early, mid and late) of the stance phase.

In one example implementation, the gait phase may be determined based on force or pressure sensors located on the lower limb device 100. For example, force sensing resistors may be provided at the heel and toe to detect heel and toe contact with the ground. Each force sensor can have a threshold associated therewith for detecting contact. The early-, mid-, and late-stance subphases, and the swing phase, can then be determined as follows:

|  | HEEL ON | HEEL OFF |
| --- | --- | --- |
| TOE ON | Mid | Late |
| TOE OFF | Early | No ground contact (swing) |

This example approach allows for the differentiation between the three subdivided states (subphases) of stance phase, and also allows for forward (clockwise through table) and backward transitions (counter-clockwise through table) between the phases and subphases. Such an implementation is suitable for gait phase tracking for both forwards and backwards walking. It will be understood that the aforementioned gait phase detection implementation is provided merely as an example, and that other methods of gait phase detection may be employed. For example, other methods of gait phase segmentation are disclosed by Lenzi (Lenzi et al., IEEE Robotics & Automation Magazine, December, 94-107, 2014).

Method of Stance Control for Lower Limb Device

According to various example implementations of the present disclosure, in which separate control algorithms are employed for swing and stance phases, a stance control method may be employed to control the actuation of one or more joint actuators during a series of stance subphases through the use of a virtual constraint in which the torque applied to each joint is enforced according to a pre-determined dependence of torque on a plurality of joint angles and walking speed.

In previous reported studies involving the use of a virtual constraint, such as the method disclosed by Lenzi (Lenzi et al., IEEE Robotics & Automation Magazine, December, 94-107, 2014), a virtual constraint stance control method was employed for the control of a powered prosthesis involving the knee joint and the ankle joint. According to the stance control method of Lenzi, each joint actuator was controlled based on a local joint angle and the measured walking speed—i.e. the torque applied to the knee joint was determined based on the local knee angle and measured walking speed, and the torque applied to the ankle joint was determined based on the local ankle angle and the measured walking speed.

Figure 2A:
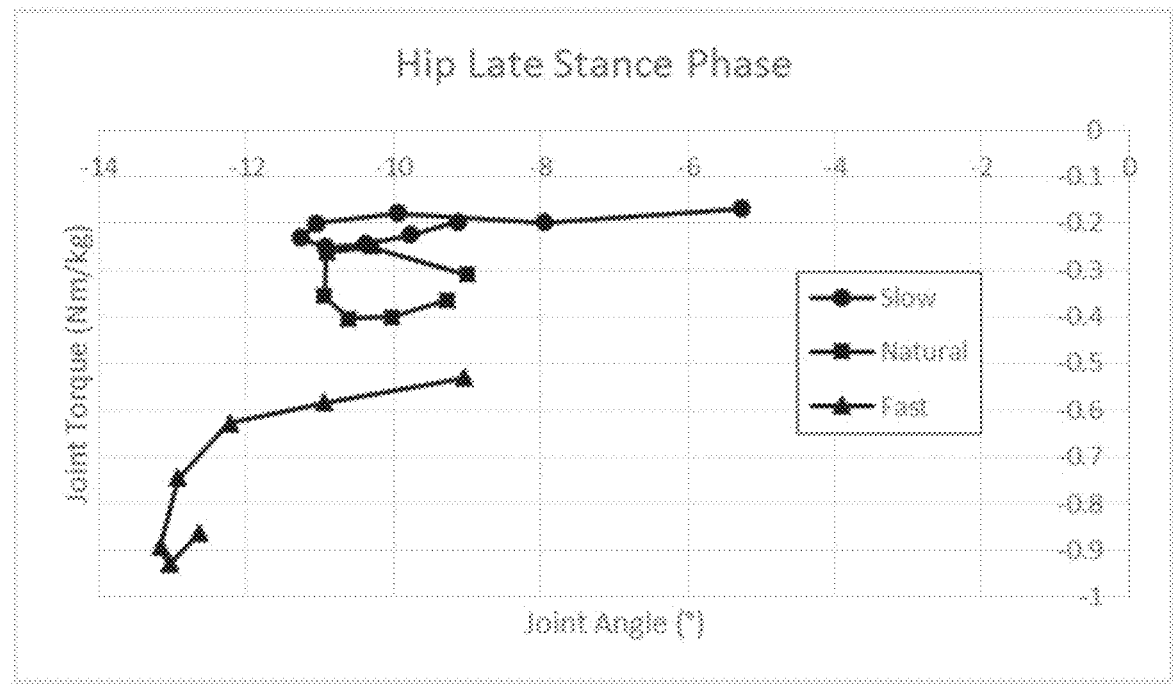
FIGS. 2A and 2B show the dependence of hip torque on local hip angle and the knee-ankle angle difference, respectively.

Although the local joint control method of Lenzi was successful in controlling a prosthesis having a knee joint and an ankle joint, the present inventors discovered that such a stance phase control scheme is inoperable when applied to control the hip joint actuator of a lower limb device having a powered hip joint. Indeed, as clearly shown in FIG. 2A, the dependence of required hip joint torque on local hip joint angle is not a function. This lack of a function relationship between hip joint torque and local hip joint angle precludes the use of the local hip joint angle as a phase variable for controlling the torque applied to the hip joint.

Figure 2B:
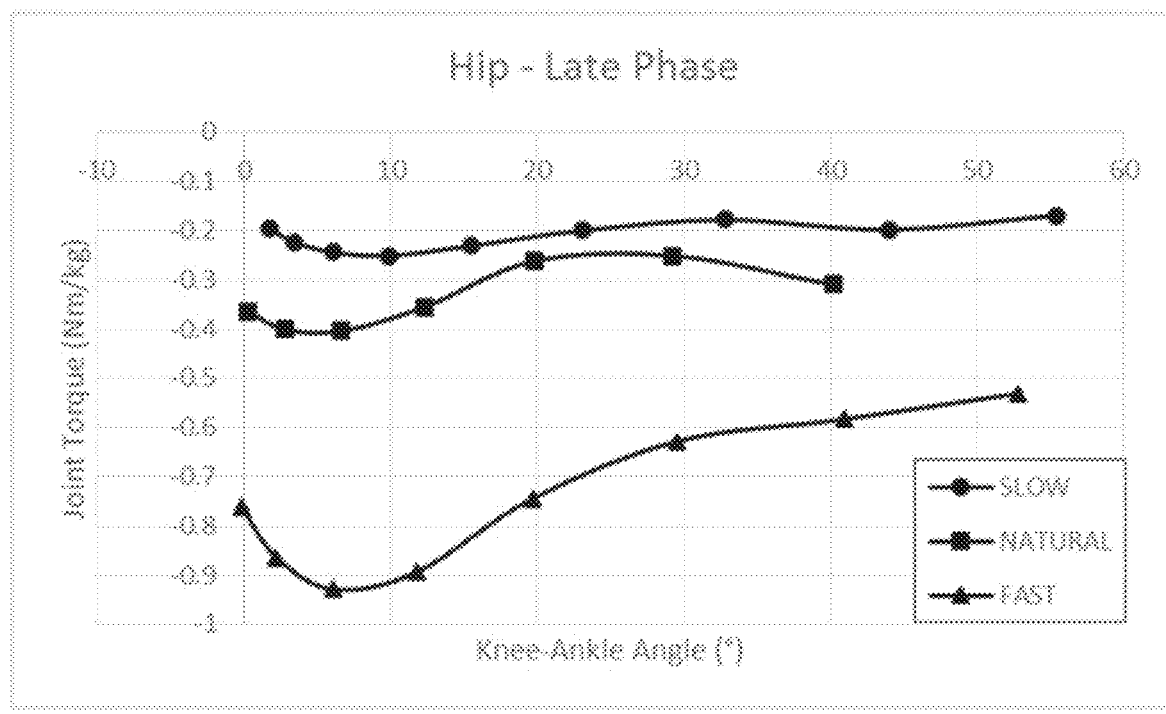

The present inventors discovered that if the difference in between the knee joint angle and the ankle joint angle is used as a phase variable, a function of hip joint torque with respect to this phase variable is obtained. For example, FIG. 2B shows the dependence of hip joint torque on knee-ankle angle for a range of walking speeds, clearly illustrating a functional relationship between hip joint torque, knee-ankle angle, and walking speed, for the late stance subphase. The inventors found that such function profiles could be obtained for each subphase of the stance phase.

It was also found that the knee-ankle angle was a suitable phase variable for controlling the torque applied to both the knee joint and the ankle joint of a lower limb device. Accordingly, the knee-ankle angle and the walking speed may be employed as global phase variables for controlling the torque applied to each joint of a lower limb device having powered hip, knee and ankle joints.

Accordingly, in one example embodiment, a method for controlling the torque applied to the hip joint involves controlling the hip joint torque by enforcing, for each stance subphase, a pre-determined dependence of hip joint torque on knee-ankle angle difference and walking speed.

In another example embodiment, a pre-determined relationship (e.g. virtual constraints) may be determined for each joint of a lower limb device, for each subphase of the stance phase, where each pre-determined relationship prescribes the torque required for each joint to produce a suitable gait according to the knee-ankle angle difference and the walking speed. For example, separate virtual constraint relationships (e.g. look-up tables) may be provided for each of the early-, mid-, and late-stance phases. Through the use of such a virtual constraint controller, the lower limb device is decoupled from following a predetermined gait trajectory. This advantage allows the lower limb device to be more able to respond to changes in environment such as terrain conditions/slopes, and changes in the user such as various joint velocities.

The dependence of torque on joint angle difference and walking speed may be determined, for example, via experiments with subjects in which joint angles, walking speed, and torques are measured, or, for example, based on published biomechanical gait data, such as the data provided in Winter (Winter, D., The Biomechanics and Motor Control of Human Gait: Normal, Elderly and Pathological, 1991). The pre-determined dependence on torque may be normalized by bodyweight, thereby providing a relationship that may be customized to a particular patient upon input of the patient's body weight.

It is noted that while the preceding example embodiment pertains to the use of the knee-ankle angle difference as the phase variable, it will be understood that other phase variables, generated based on the knee-ankle angle difference, may alternatively be employed. For example, other functions may be generated, that are dependent, at least in part, on the knee-ankle angle difference, while providing a functional relationship with joint torque.

Figure 3:
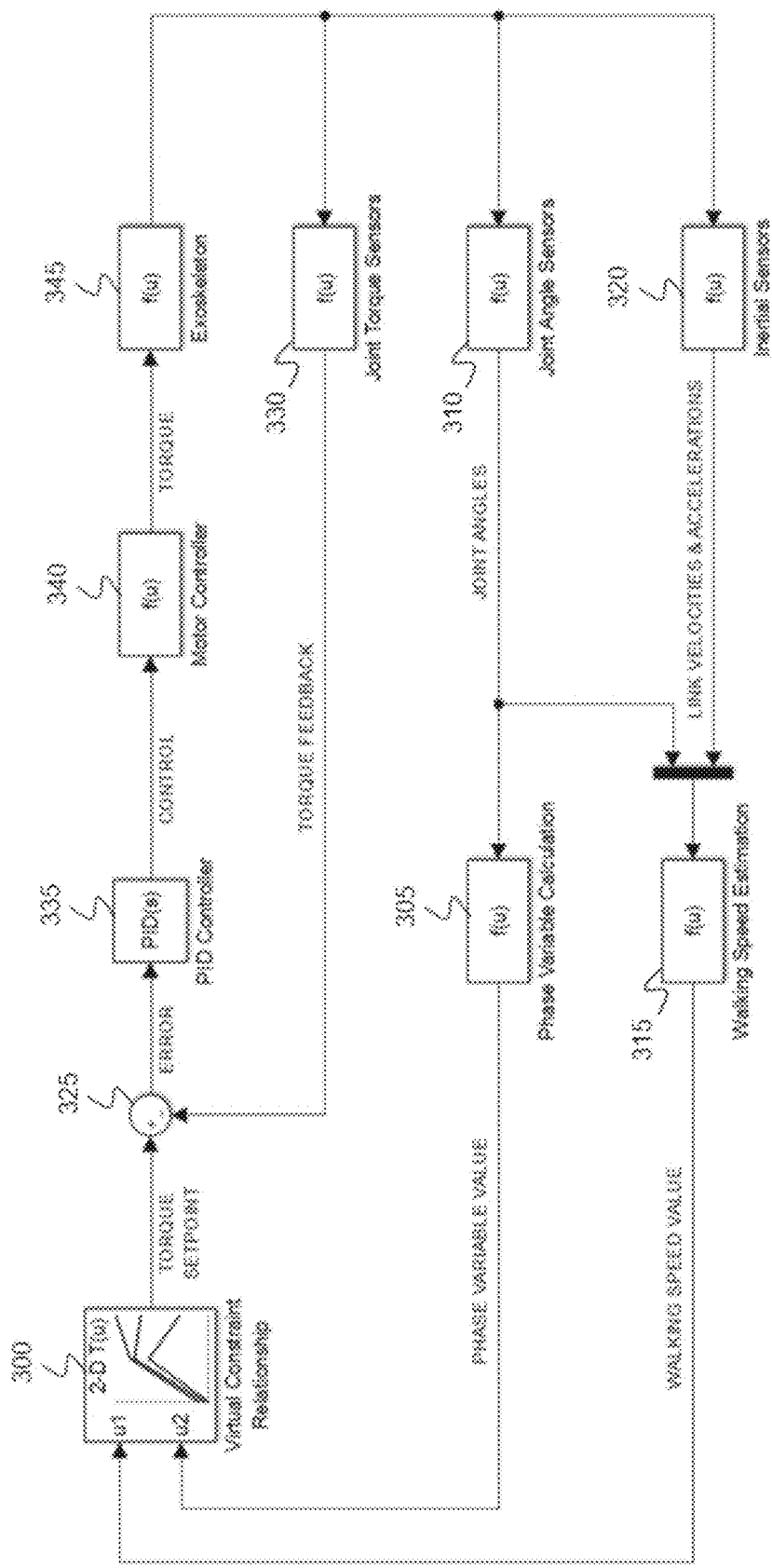
FIG. 3 shows an example stance phase control method.

Referring now to FIG. 3, an example control algorithm is provided for stance control according to a virtual constraint that employs joint angle difference as a phase variable. A pre-determined dependence of applied joint torque on an angle-difference based phase variable and the walking speed is provided as a constraint on torque, as shown at 300. The inputs to this constraint are the phase variable 305, which is determined based on joint angle sensors 310, and the walking speed estimation 315, which is determined based on input from inertial sensors measurements as shown at 320. As shown in the figure, the joint angle sensor measurements may be employed, along with the inertial sensors, in order to estimate the walking speed at 315. The torque setpoint, determined according to the constraint 300, is compared at 325 to the measured joint torque 330, and a control system (e.g. a PID control system as shown at 335) is employed to control the motor controller 340 in order to produce the desired applied torque via actuation of the joint actuator, shown at 345. The joint torque may be measured, for example, using sensors such as strain gauges. Alternatively, the joint torque may be indirectly determined by monitoring a current applied to the actuator motor.

The constraint 300 may be provided as a lookup table for interpolation during implementation. For example, lookup tables may provide torque values for each controlled joint that are valid for walking speeds ranging between 0.5 m/s and 1.75 m/s, thus allowing for natural preferred gait of 1.4 m/s along with slower and faster walking speeds. The use of the walking speed as a lookup variable allows for a wide range of applicable walking speeds through torque modulation.

Although the preceding example implementation pertained to the control of all joints of a lower limb device having powered hip, knee and ankle joints, it will be understood that the preceding example method may be adapted to control a wide variety of lower limb devices.

In one example embodiment, the aforementioned stance control method may be adapted to control only the hip joint (or hip joints) of a powered lower limb device. For example, if a lower limb device includes a powered knee and a powered ankle joint in addition to a powered hip joint, then the stance control method may be employed to control the hip joint, while other control methods (such as based on local angle measurement) may be employed to control the knee and ankle joints. In another example embodiment, a lower limb device may include a powered hip joint in the absence of powered knee and ankle joints. In such an implementation, local angle sensors associated with the unpowered joints may be employed to provide the angle sensing inputs to the virtual constraint controller for the powered hip joint.

In some example embodiments, the aforementioned stance control methods may be adapted to control the torque applied to a first joint of a lower limb device according to a virtual constraint that is dependent on the walking speed and phase variable constructed from the local angles associated with a second joint and a third joint. The phase variable may be dependent on the difference between the joint angles of the second and third joints.

As noted above, the present method was discovered based on the need to solve a technical problem in which the absence of a functional relationship between a local angle of a given joint and a torque applied to the given joint, where a functional relationship between torque and a phase variable was obtained by employing a phase variable involving a difference between two joint angles. The local angles may be associated with joints other than the given joint, as in the case of the example implementation in which the hip joint torque is controlled according to the difference between the knee and ankle joint angles.

A benefit of the aforementioned stance control method is that patient-specific tuning, other than inputting the patient's weight, is reduced or eliminated through the angle-torque relationship, which is independent of joint velocities that vary across patients. Furthermore, by interpolating the profiles based on walking speed, the requirement for speed-specific tuning is eliminated. This secondary feature of the control system allows for a more involved rehabilitation session in a similar time frame to that of other exoskeletons, as a therapist should not need to spend significant time tuning the exoskeleton.

The present example stance control method varies in several key aspects from the predetermined gait trajectory controllers currently used for rehabilitation exoskeletons. Notably, the present control methods provide an autonomous control strategy. This autonomous structure is inherently more robust to disturbances as there is no push to re-synchronize with time. Secondly, the joint level controllers enforce torque, as opposed to position, during stance phase.

As noted above, the choice of a joint angle difference as virtual constraint for this controller is also unique when compared with other controllers. The angle-difference constraint is the mathematical difference and requires only local joint data. In comparison, the center of pressure constraint implemented in prosthesis control by Gregg et al. (Gregg et al., IEEE Transactions on Robotics 30, 1455-1471, 2014) requires Cartesian coordinates and interaction forces for implementation. Local angles are significantly easier to sense compared to Cartesian coordinates, and interaction forces would require a 3-DOF load cell at the minimum. The simplicity of sensing the required data and the mathematical simplicity of calculation are thus benefits of the present virtual constraint method based on a joint angle difference as a phase variable.

The present control method differs greatly from conventional practice in commercial powered orthoses, which presently employ predetermined gait trajectory control. Such conventional implementations track a recorded motion, typically from known able-bodied "normal" walking, in an attempt to reproduce natural gait. In contrast, the example control methods disclosed herein employ a phase variable to determine the torque required to continue motion during various subphases of the stance phase of the gait cycle. The present autonomous control methods may be beneficial in providing more robust control, as the requirement for synchronization with time is eliminated.

Moreover, the present example methods of stance control differ from previous implementations that employ holonomic virtual constraints. In previous implementations involving virtual constraints in the field of bipedal robotics, a kinematic relationship (i.e. only position information) between an input variable and multiple output parameters, such as joint angles, is employed. Such methods have been employed by Westervelt et al., for example, to determine joint angles based on the angle of a virtual link connecting the hip and ankle (Westervelt et al., Feedback Control of Dynamic Bipedal Robot Locomotion, 2007). However, the present example stance control methods differs from such approaches, as the present example methods employ a direct relationship between joint angle (input) and joint torque (output), as opposed to an indirect relationship mediated through a holonomic virtual constraint.

Finally, as noted above, the present control method differs significantly from the control method disclosed by Lenzi et al. (Id.). In Lenzi's stance phase control, the local joint angle (i.e. ankle or knee) is employed to determine the corresponding local joint torque. As described above, the present inventors have found such an implementation to be inoperable for control of the hip joint, due to a lack of a function relationship between the hip joint torque and the local hip angle. In contrast, when the present stance phase control method is applied to control a hip joint actuator, the difference in the knee-ankle angle is employed as a phase variable to provide a virtual constraint that is a function for controlling the hip joint torque. Moreover, as described above, the phase variable based on the difference between the knee angle and the ankle angle may be employed as a global phase variable for controlling the torque applied to the knee and ankle joints.

Method of Swing Control for Lower Limb Device

A minimum jerk trajectory is often used in path planning as it is analogous with the smoothest possible path for an object to travel though. Traditionally, a minimum jerk trajectory is calculated beforehand (a priori) according to the initial position and desired final position and time duration as shown in equation (1) from Flash & Hogan (Flash & Hogan, The Journal of Neuroscience, Vol 5(7), pp. 1688-1703, 1985:

$$P(t)=Pi+(Pi-Pf)*(15*T^4-6*T^5-10*T^3) \quad (1)$$

where: P(t)—position, Pi—initial position, Pf—final position, T—normalised time=(t/tf). This path can then be used to control the motion of an object, such as the joint(s) of a lower limb device, using a control system. Such known jerk minimization swing control methods therefore employ a precalculated minimum jerk trajectory.

Figure 4A:
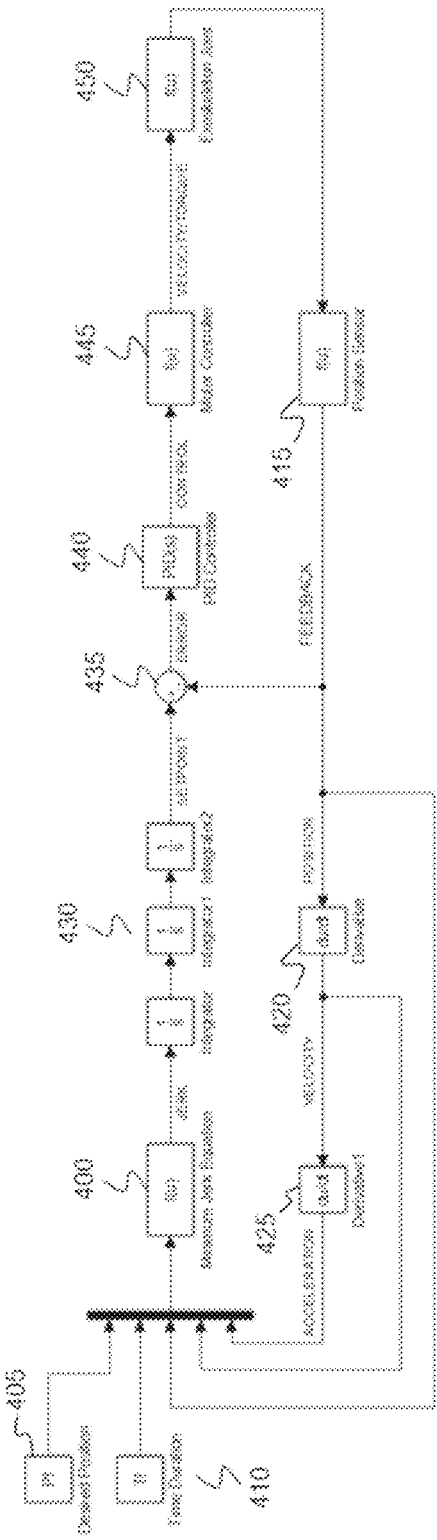
FIGS. 4A and 4B show example swing phase control methods.
Figure 4B:
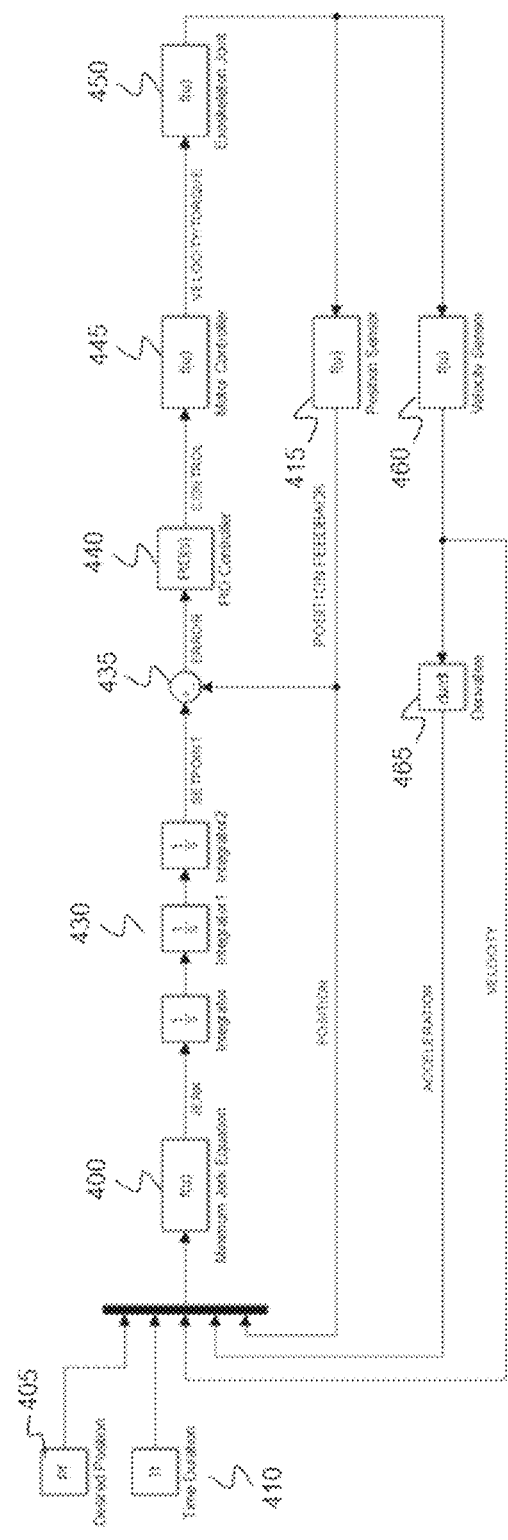

Referring now to FIGS. 4A and 4B two example algorithms are shown for controlling the swing phase of a lower limb, in which a feedback-based minimum jerk trajectory control scheme is employed for control of the swing phase of gait. This method enables the controller to respond to disturbances in real-time with a minimum jerk trajectory.

Unlike previously implemented swing phase control methods, the example method illustrated in FIG. 4A involves the calculation of a swing trajectory based on a minimum jerk calculation at each time point in real time. The general equation (2) from Liu & Todorov (Liu & Todorov, The Journal of Neuroscience, Vol 27(35), pp. 9354-9368, 2007), shown below, demonstrates this calculation of jerk according to input of current position, velocity, and acceleration of the joint, as well as the remaining time of the trajectory:

$$J(t)=(60/(D^3))*(Pf-P(t))-(36/(D^2))*V(t)-(9/D)*A(t) \quad (2)$$

where: J(t)—calculated minimum jerk, D—remaining time=(tf−t), Pf—final position, P(t)—current position, V(t)—current velocity, A(t)—current acceleration. This equation is derived from a minimisation problem and it thus produces the minimum jerk at each time point. In order to produce a trajectory, this equation is integrated three times in order to determine the position setpoint for the trajectory.

An example implementation of this method is shown in FIG. 4A, as explained herebelow. As shown at 400, the minimum jerk equation, such as equation (2) above, which is dependent on position, velocity and acceleration, is provided with the desired position 405, the desired time duration 410, and the measured inputs of position 415, velocity 420, and acceleration 425. The minimum jerk equation is processed to calculate the minimum jerk at 400, and integrated via the three integration operations 430 in order to generate a new real-time position setpoint.

This position setpoint is compared at 435 with the measured position 415 to determine a position error, which is employed, via a controller 440 (such as a PID controller), to control the motor controller 445. The motor controller 445 employs an internal PID loop (not shown) to ensure either the required velocity or torque to move the joint to the setpoint is realized by the joint, as shown at 450. The internal PID loop on the motor controller enables a determination of the velocity/torque required to move towards the desired angle, and the main feedback loop will reduce this velocity/torque according to the error between current and desired positions, ensuring that the correct torque/velocity is applied to the joint, while the main PID loop calculates the required torque/velocity to move the joint towards the desired setpoint. In this way, the main loop ultimately controls the position of the joint, while the internal loop regulates the torque applied during motion.

FIG. 4B illustrates an alternative example implementation, in which a velocity sensor 460 is employed to measure the velocity of the joint. This method is expected to allow for higher fidelity acceleration calculation 465, as the second numeric derivative tends to be of low fidelity due to propagation of error.

Unlike minimum jerk swing control methods known in the art, such as the method disclosed by Lenzi et al. US Patent Application Publication No. US20160058582, jerk is minimized while traversing between a given starting and ending point using a feedback loop that regulates jerk, rather than position. More specifically, the method disclosed by Lenzi et al. regulates jerk at a given point in time according to a specific position that is computed prior to beginning of the swing phase. After selecting a given starting and ending point and a required duration of time, Lenzi et al. calculates the position vs. time profile that minimizes jerk, thereby providing a position profile which is enforced during the swing phase via a feedforward and feedback loop. In contrast, according to the present example swing phase control method, a given start and ending point and a required duration of time are selected, but a position profile for the swing phase is not calculated. Instead, a feedback loop is employed to determine, in real-time, the appropriate torque that will minimize the jerk for the remainder of the swing phase, while still achieving the required end-point at end-time, based on the current point/velocity/acceleration measurements.

By using a minimum jerk trajectory, the swing controller is able to provide a smooth motion independent of the stance phase controller. At the end of stance phase, the current joint angle, velocity, and acceleration are simply used as inputs to swing phase controller, thus allowing the swing controller to function regardless of the previous stance phase performance. In order to allow for proper foot clearance, a maximum knee angle may be enforced as a target point in the trajectory. The swing duration is calculated in proportion to the stance phase duration based on able-bodied biomechanics. The minimum jerk trajectory, generated according to the real-time feedback method described above, is capable of responding to external disturbances in a minimum jerk trajectory thereby ensuring smooth motion throughout swing.

Figure 5:
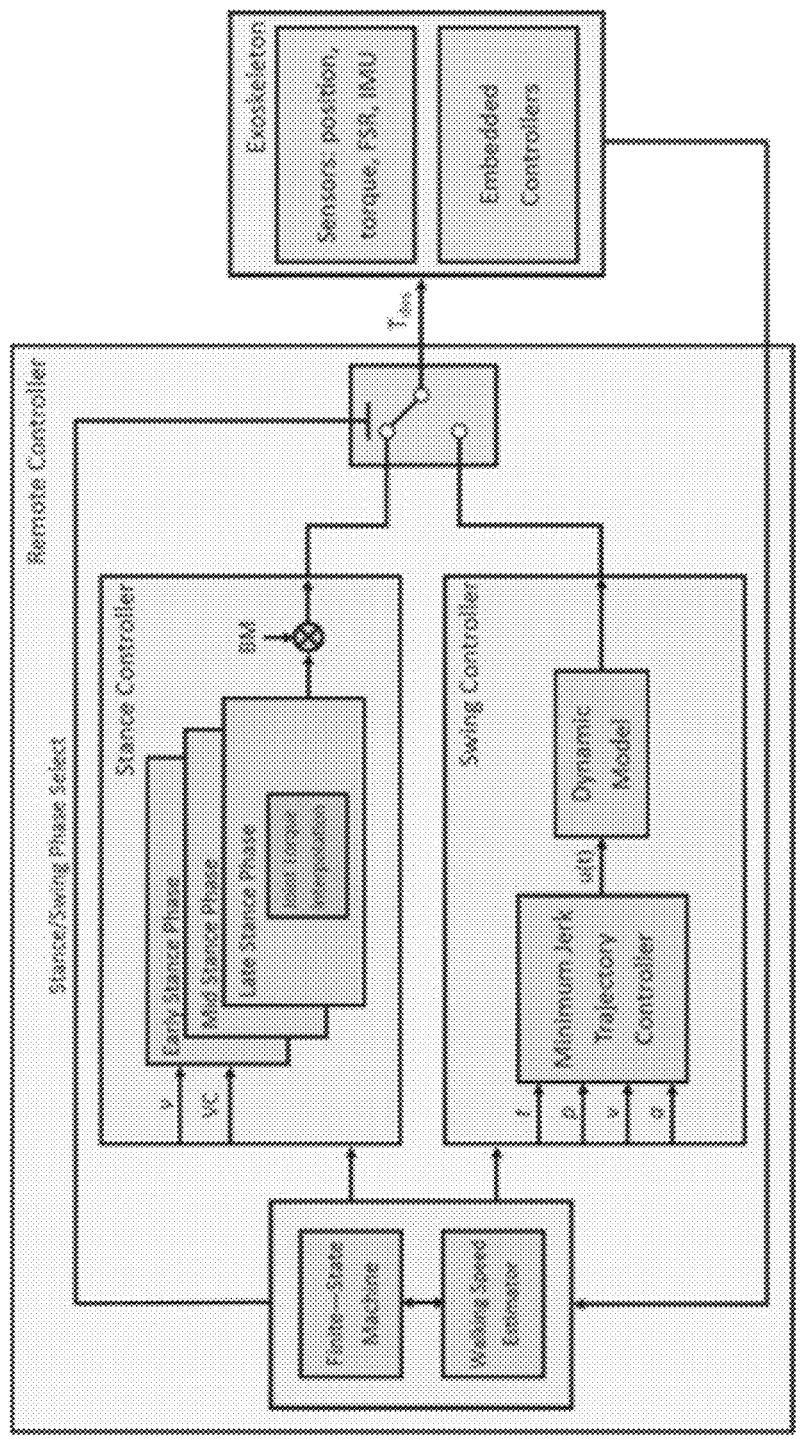
FIG. 5 shows an example gait control method involving stance and swing phase control

In some example implementations, the aforementioned stance phase control method may be employed with the aforementioned swing phase control method, in order to provide control system suitable for controlling the complete gait cycle. An example implementation of such a combined control method is illustrated in FIG. 5. In other example embodiments, the aforementioned stance control method may be combined with a different swing phase control method, or the aforementioned swing phase control method may be combined with a different stance phase control method.

Although the preceding example implementations pertained to the control an orthotic lower limb device, it will be understood that the present stance control embodiments may be readily adapted for the control of prosthetic and robotic devices.

Modular Actuator for Lower Limb Device

Referring again to FIG. 1A, the example lower limb actuator 100 is formed from a plurality of joint assemblies 110A, 110K and 110H in a modular fashion. As can be seen from the figure, a common actuator mechanism is employed to power each of the hip, knee, and ankle joints in the sagittal plane.

The knee joint assembly 110K is linked to the ankle joint assembly 110A and the hip joint assembly 100H by respective connection rods 130 and 135. Such connection rods may be formed, for example, as hollow tubes formed from carbon fiber. As described in further detail below, the joint assemblies are configured to receive and secure ends of the connection rods 130 and 135 such that the inter-joint distance is adjustable, thereby allowing adjustment of the modular lower limb device so the axis of rotation of each actuated joint is aligned with each respective anatomical joint of the device wearer. Once adjusted, the joint-to-joint length may be locked, after which the lower limb device may transfer its weight to the ground.

Figure 6A:
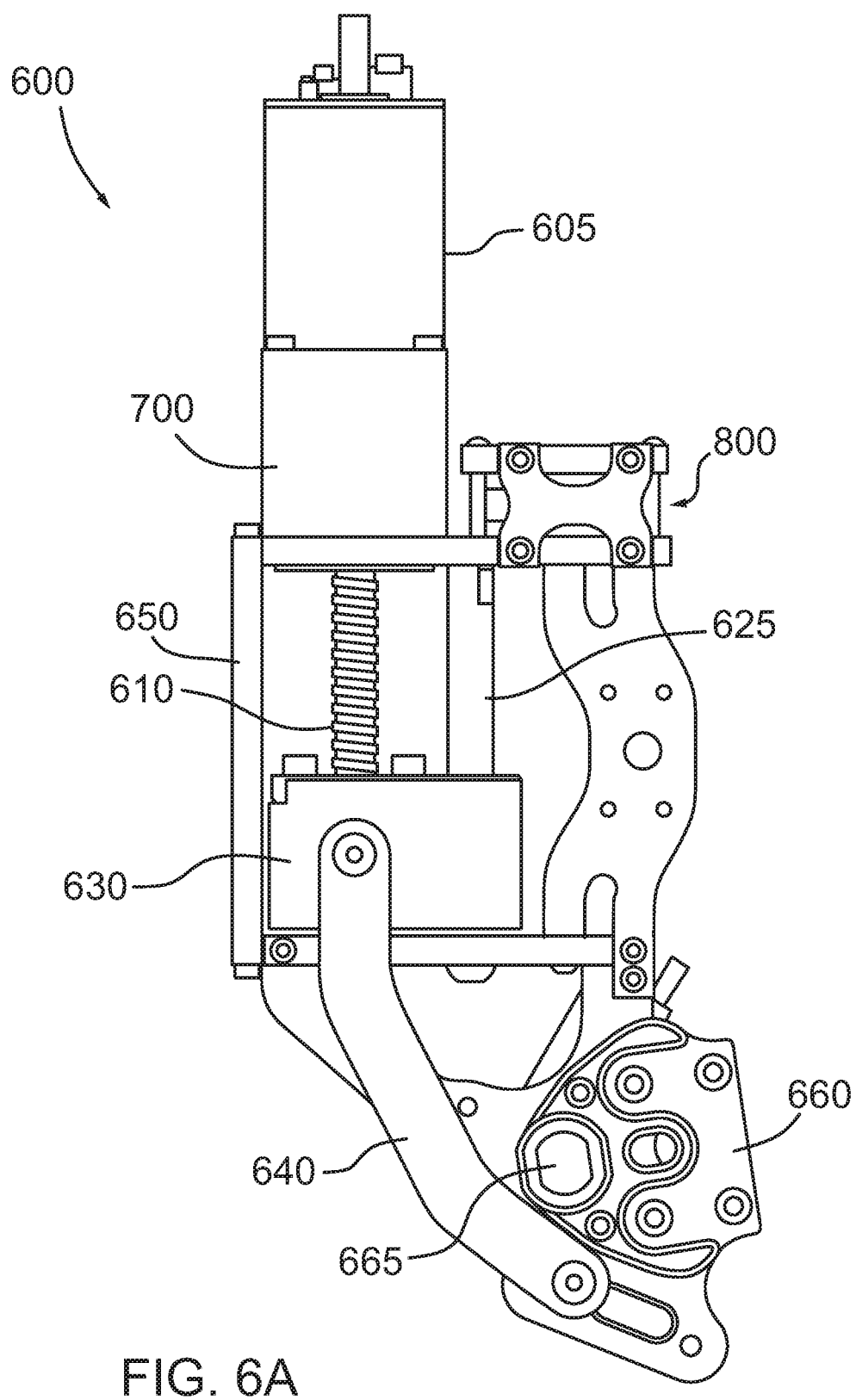
FIGS. 6A and 6B show an example joint assembly for forming a modular lower limb device.

FIG. 6A illustrates a joint assembly 600 for use in forming a powered lower limb device, such as the lower limb device shown in FIG. 1A. Accordingly, a plurality of such joint assemblies 600 can be employed for different joints, such as the hip, knee, and ankle joints. The joint assembly 600 employs a reconfigurable offset slider-crank mechanism, which takes advantage of the varying range of motion between each joint to provide for more speed or torque as appropriate.

Figure 6B:
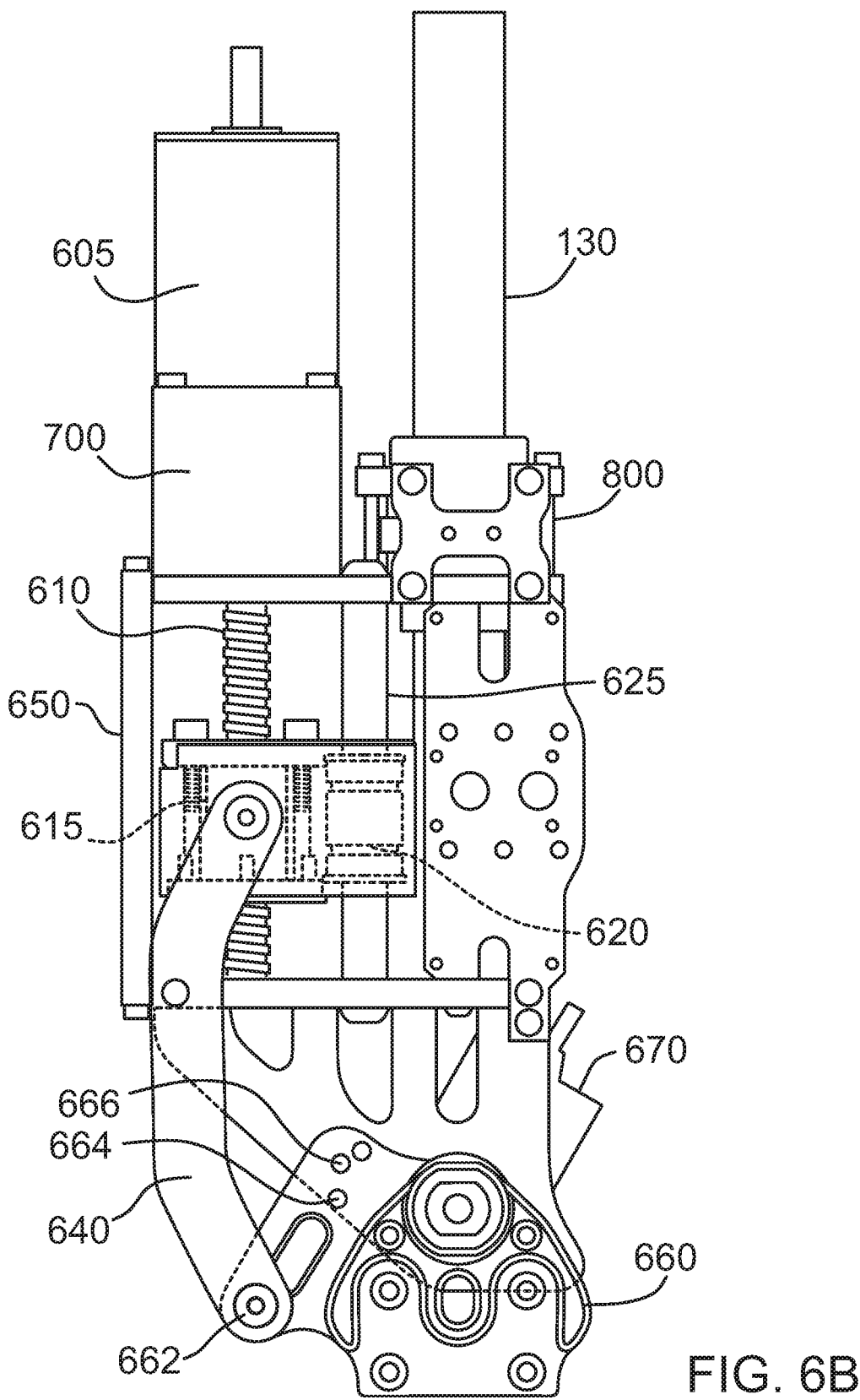

As shown in FIG. 6A, the example joint assembly 600 is powered by a motor 605, such as a brushless DC motor. The non-rotating portion of the motor 605 is supported on a rigid support frame 650, and a crank 660 is pivotally coupled to the support frame 650 through a joint pin 665, thereby forming a joint. An output shaft (not shown in FIG. 6A) associated with the motor 605 is coupled, through a coupling housed within housing 700, to a screw 610, which, through its associated nut (not shown in FIG. 6A), converts rotary to linear motion. An example implementation of the coupling is described in further detail below. The crank 660 is mechanically coupled, either directly, or indirectly (as shown in FIGS. 6A and 6B), to a nut provided on the screw 610 via a coupling link 640, such that linear actuation of the nut by the motor responsively produces rotation of the crank about the joint. The output shaft associated with the motor 605 may be a motor shaft or an output shaft of a gearbox.

In the example embodiment shown in FIGS. 6A and 6B, the screw-based linear actuator is implemented as a ball screw and a ball nut. The ball nut actuates the slider joint, generating axial forces with response to input torques on the ball screw 610. The high transmission efficiency renders the mechanism backdrivable, such that that an input axial force on the ball nut will result in the rotation of the ball screw. It will be understood, however, that a wide range of alternative configurations may be employed, such as lead screws, roller screws, and differential roller screws.

Figure 6C:
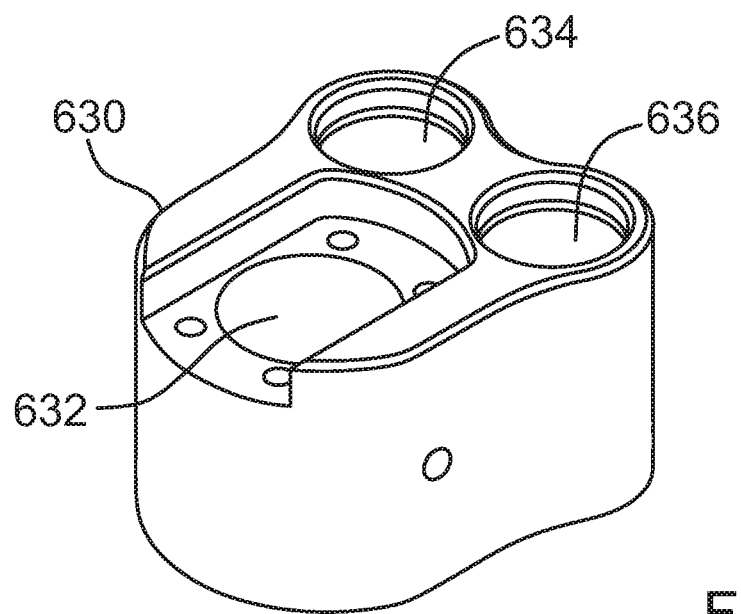
FIGS. 6C and 6D show an example guidance member for guiding a nut and bearings.
Figure 6D:
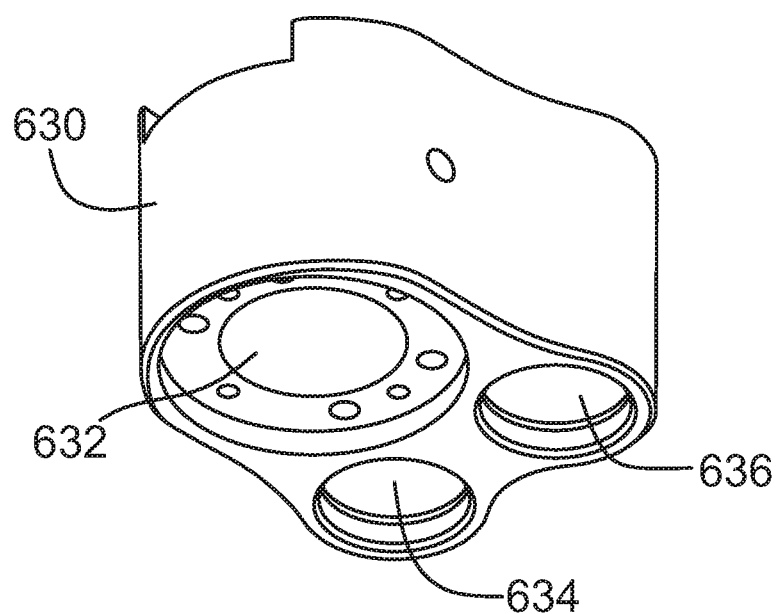

In the non-limiting example embodiment shown in 6B (which shows a partially transparent view), the ball nut 615 is fastened to support axial loads exclusively, with the support coming from two linear ball bearings 620 on two linear shafts 625 parallel to the ball screw 610. According to this example implementation, the slider joint consists of a guide member 630 that is shown in FIG. 6A, and in FIGS. 6C and 6D. The ball nut 615 is attached to the guide member 630 (shown in FIG. 6A) and within aperture 632 (shown in FIG. 6C), and the two linear ball bearings 620 are respectively retained within apertures 634 and 636 (shown in FIG. 6C) of the guide member 630 by retaining rings. As shown in FIG. 6A, the coupling links 640 of the slider-crank mechanism are also joined to the guide member 630, and to the crank 660, by the combination of shoulder bolts and corresponding diameter bushings (such that the coupling link 640 is indirectly coupled to the ball nut via the guide member 630). These provide proper bearing interfaces for the rotating surfaces between coupling link to slider joint, and coupling link to crank. The two coupling links 640 in turn transmit forces generated forces in the slider joint, down to the crank 660. The crank 660 is preferably positioned, during use, to be aligned with or near the user's joint axis, in order to prevent, reduce or minimize undesired joint reaction forces. In the example embodiment shown in FIGS. 6A and 6B, the two cranks 660 are provided, with one on each side of the mechanism, and are fixed to rotate together through the joint shaft. In the example embodiment shown in FIG. 6A, the joint interface 665 consists of a double D shaft and accordingly shaped hole in the crank 640. Rotation of the crank 660 and joint shaft relative to the static frame 650 is facilitated through two flanged bushings.

One or more sensors may be provided on (attached to) the joint assembly 600, such as angle sensors, force sensors, and inertial sensors. As shown in FIG. 6B, an angle sensor 670 is integrated with the joint assembly to provide an angle sensing signal.

Figure 6E:
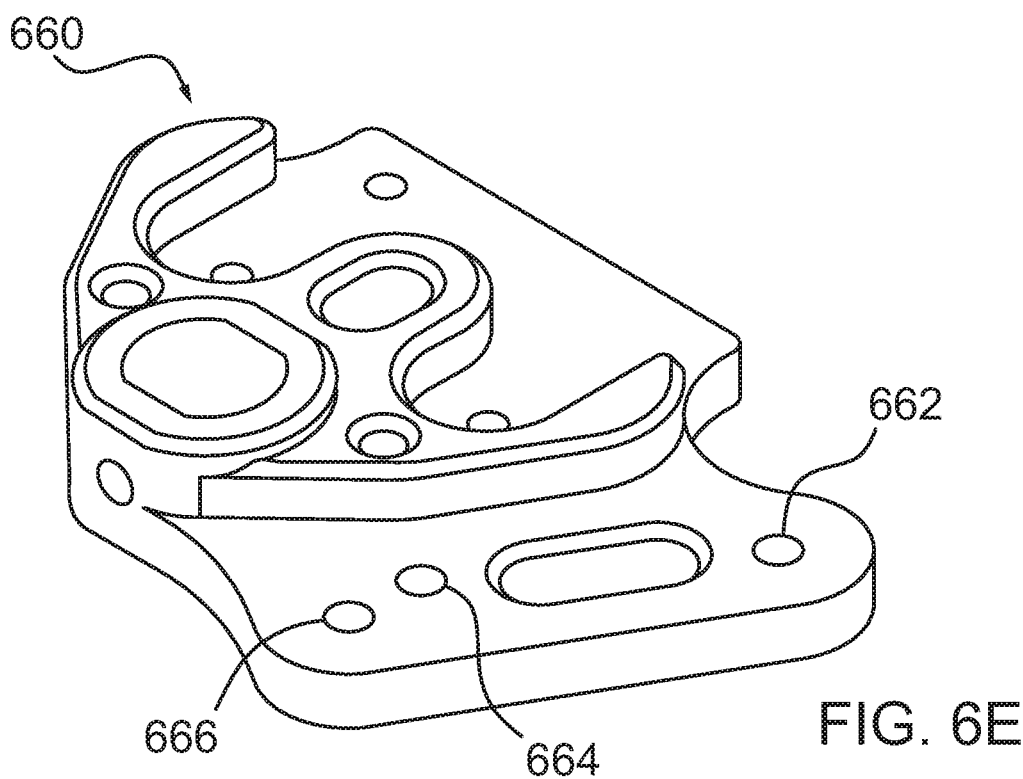
FIG. 6E shows an example crank with multiple anchor points.

The crank 660 may include a plurality of selectable anchor points for selective, and optionally reconfigurable, connection of the distal portion of the coupling link 640. For example, as shown in FIG. 6E, the crank 660 includes three selectable anchor points 662, 664 and 666, where FIG. 6B shows an example configuration in which the coupling link 640 is connected to anchor point 662. These anchor points vary the lever arm associated with the slider-crank mechanism, thereby permitting the selection of a different range of rotational travel, rotational speed, and torque. Such changes the effective lever arm provide more or less rotational travel, at the expense of torque.

In one example embodiment, the selectable anchor points of the crank 660 may be configured to provide a respective range of rotational travel, rotational speed, and torque that is customized for a respective anatomical joint. Accordingly, the joint assembly 600 can be reconfigured to permit the selection of a suitable anchor point of the coupling link to the crank in order to configure the joint assembly for different use in actuating a desired anatomical joints. A set of such joint assemblies, each having a common mechanical design, may thus be individually configured for actuating different anatomical joints, and assembled in a modular fashion to form a powered orthotic (e.g. exoskeleton), prosthetic, or robotic device.

Figure 7A:
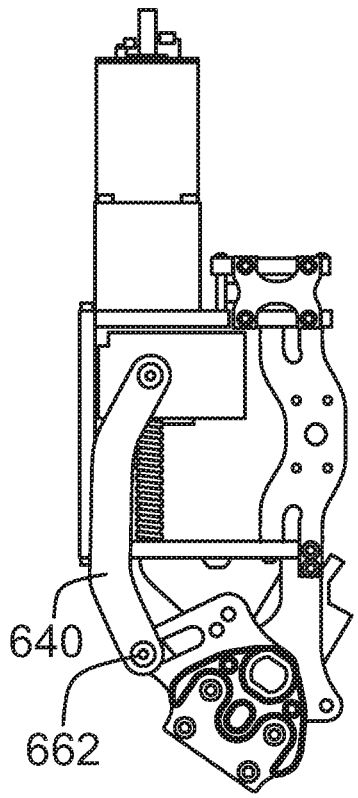
FIGS. 7A-B, 8A-B and 9A-B show joint assemblies configured for the ankle, knee and hip joints.
Figure 7B:
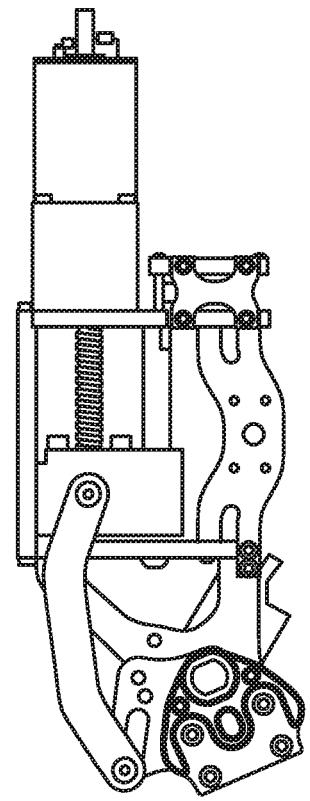
Figure 8A:
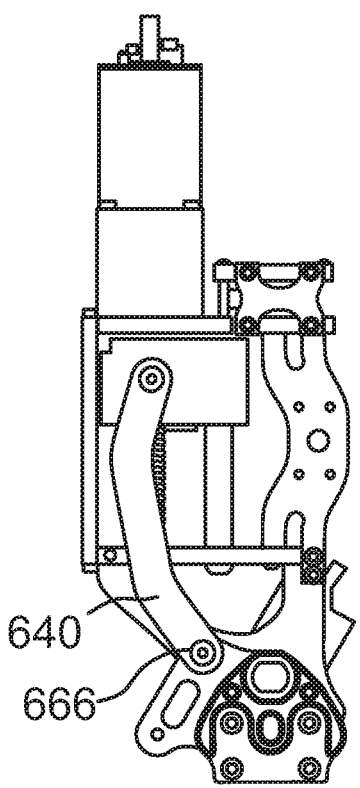
Figure 8B:
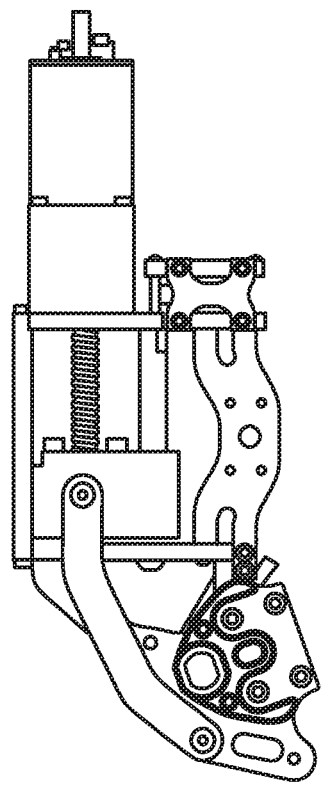
Figure 9A:
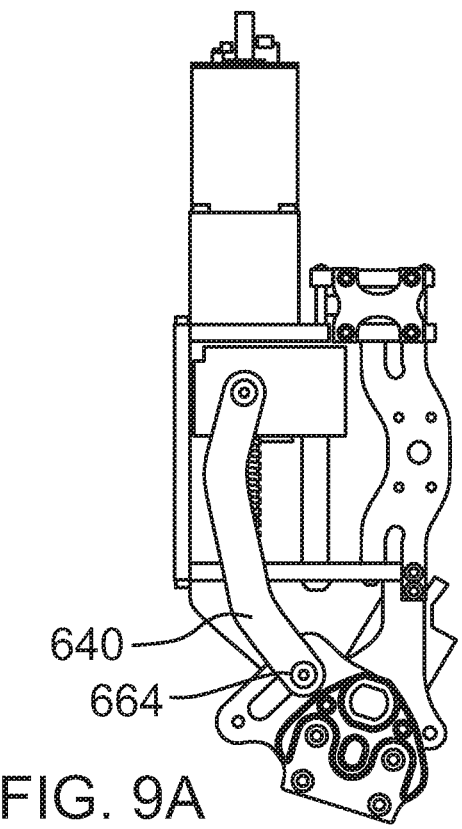
Figure 9B:
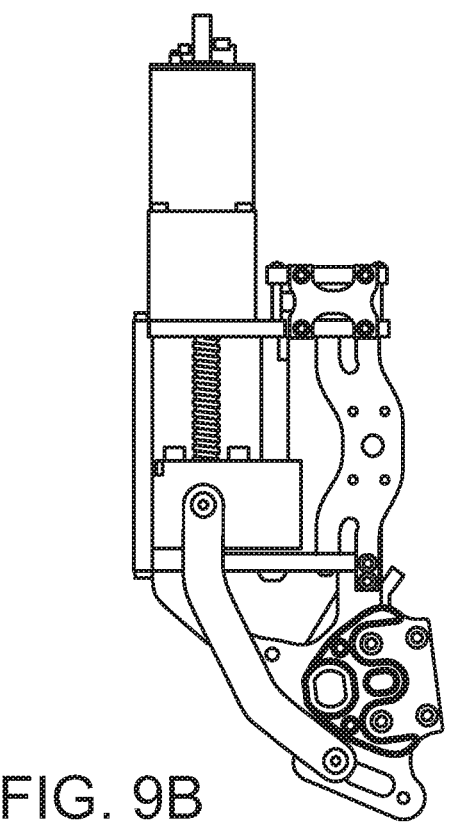

FIGS. 7A-B, 8A-B, and 9A-B illustrate the configuration of the joint assembly of FIGS. 6A-B according to the actuation properties and requirements of different anatomical joints. In the example configuration shown in FIGS. 7A and 7B, the joint assembly 600 is customized for the actuation of an ankle joint, in which the coupling link 640 is connected to anchor point 662, where FIGS. 7A and 7B show the two limits of the range of rotational motion. In the example configuration shown in FIGS. 8A and 8B, the joint assembly 600 is customized for the actuation of a knee joint, in which the coupling link 640 is connected to anchor point 666, where FIGS. 8A and 8B show the two limits of the range of rotational motion. In the example configuration shown in FIGS. 9A and 9B, the joint assembly 600 is customized for the actuation of a hip joint, in which the coupling link 640 is connected to anchor point 664, where FIGS. 9A and 9B show the two limits of the range of rotational motion.

As the ankle joint requires larger torque requirement than the hip and knee, while also a smaller range of motion, the anchor point 662 employed in FIGS. 7A-B is located further from the joint axis than the anchor points in FIGS. 8A-B and 9A-B. In the ankle configuration, the lever arm is 50 mm allowing for 175 Nm of peak torque and a rotational travel of 57.5 degrees. While for the knee configuration, a maximum travel of 110 degrees is achieved with peak torques of up to 100 Nm. The hip is kinematically similar to the knee but with a 10 degree offset. The design is inherently safe due to the fact that each joint is mechanically limited within the human range of motion. In some example implementations, the anchor points may be configured as follows:

|  | Min Torque (Nm) | Max Torque (Nm) | Range of Motion (deg) | |
|---|---|---|---|---|
| Ankle | ~0.2 | ~175 | 22.5 dorsiflexion | 35 plantarflexion |
| Knee | ~0.1 | ~100 | 0 extension | 110 flexion |
| Hip | ~0.1 | ~95 | 17.5 extension | 98 flexion |

In one example implementation, these maximum torque values all translate to the same thrust load of 3500 N, which is established as the maximum operating load. The actuator is actually limited by the bearings which can support up to 4400 N (the ball screw is up to 5800 N), while the motor could produce a maximum of ~5500-6000 N.

Compact Coupling Mechanism

Figure 10:
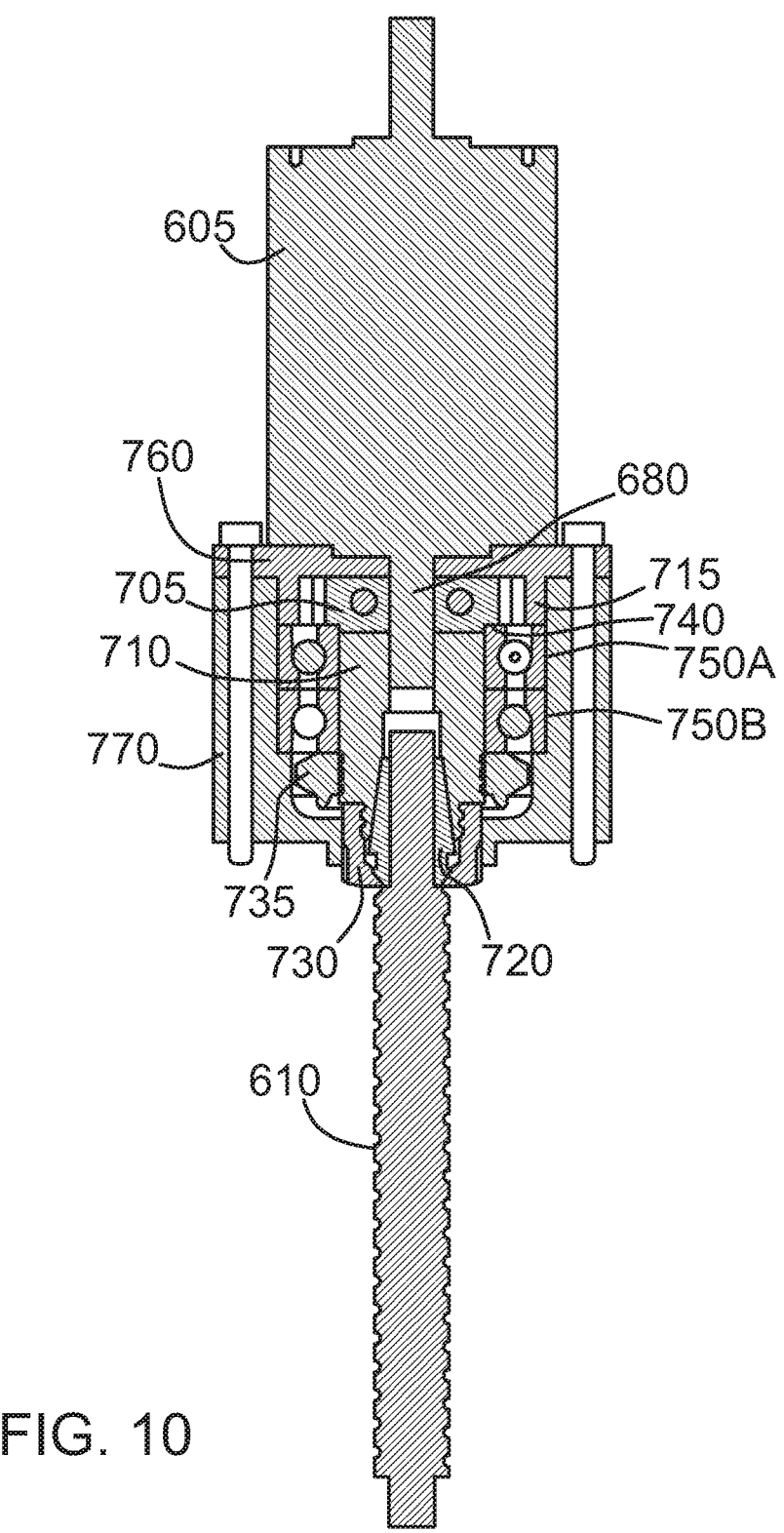
FIGS. 10 and 11 illustrate an example coupling device for coupling an output shaft of a motor to a ball screw.
Figure 11:
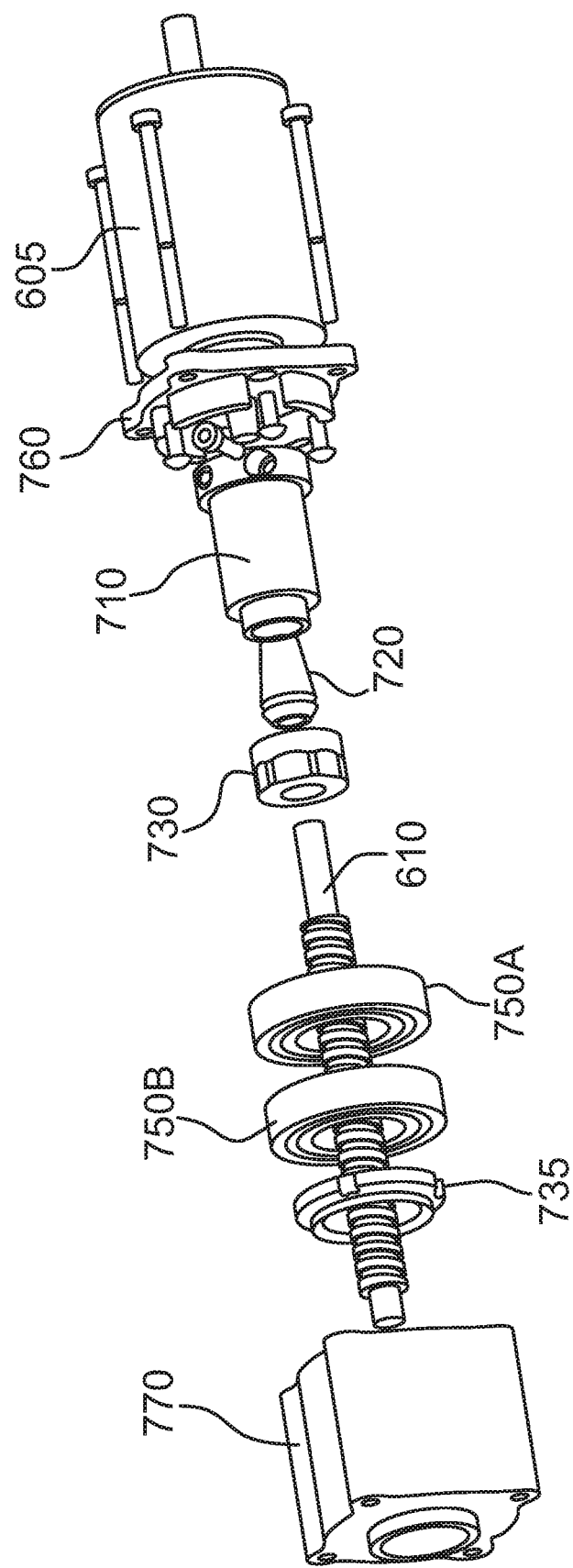

In one example implementation, in order to protect the weak bearings inside the brushless motor from the axial loads generated, a ball screw support mechanism may be employed. Such a ball screw support solution may be made compact through the design of a mechanical coupling (between motor shaft and ball screw), which allows for angular contact bearings to be placed on the outer diameter of the coupling. This configuration allows for the use of larger diameter angular contact bearings, as opposed to conventional coupling methods in which the bearings are placed along the ball screw shoulder. An example implementation of such a coupling is shown in FIG. 10, and an exploded view in FIG. 11.

The brushless DC motor 605, given appropriate feedback, allows for speed and torque control of its output shaft 680. The output shaft 680 is directly coupled to the miniature ball screw 610 through a mechanical coupling 710, having an internal bore. The coupling 710 offers two different shaft to hub interfaces. On the motor (proximal) side, the proximal end 705 of the coupling 710 is split, and two bolts are used to clamp the coupling 710 to the motor shaft 680 for torque transfer through frictional force. The head of the two bolts rest within counter-bores in the coupling shoulder 715, which play a beneficial role during assembly, as noted below.

On the ball screw (distal) side, the distal end of the coupling 710 features an 8 degree tapered bore, for use with a collet 720, such as an ER collet. With the ball screw shoulder inserted, tightening a standard collet nut 730 against the ER collet 720 pushes it further into the tapered cavity, greatly increasing the interface pressure and frictional force. This locking mechanism ensures proper shaft to hub interface for the transfer of torque, axial load, while maintaining ball screw alignment.

As the motor torque is transmitted to the ball screw through the coupling, the ball nut then converts this torque to a linear force. This bidirectional axial load is then transmitted back through the collet 720 and to the coupling 710. When the ball screw is in tension, the coupling shoulder 740 resting against the inner ring of the angular contact bearing 750A transmits the load to the bearing housing. When in compression, the bearing lock nut 735 that rests against the inner ring of the other angular contact bearing 750B transmits the load to the motor mounting plate 760, which, together with the distal bearing housing portion 770, forms the coupling housing 700 shown in FIG. 6A. The motor mounting plate 760 is secured with four socket head screws that clamp the motor mounting plate and distal bearing housing 770 to the frame. The alignment of the support assembly to the frame is assured through the geometric extrusion on the bearing housing.

The counter-bores (with no bolts inside) may be used to prevent rotation of the coupling 710 during tightening of the bearing lock nut 720 and collet nut 725. This is achieved by placing two solid shafts within them (e.g. having a diameter of 5.95 mm), which extends between the bearing shoulder extrusions of the motor mounting plate.

In some example embodiments, angular contact bearings are employed to handle high axial load. The example embodiment shown in FIG. 10 (2 bearing on coupling) provides a compact, small to medium load application. In some example embodiments, the angular contact bearings could be replaced by deep groove ball bearings for cost saving reasons.

Although the present example coupling embodiment is illustrated in the context of driving a ball screw assembly for use in a lower limb device, it will be understood that the present coupling device may be employed for a wide variety of other uses, and to drive different types of secondary shafts. For example, the coupling device could be employed to drive a device other than a screw & nut, thereby supporting only radial loads (the coupling could use a different secondary shaft-hub interface at this point, i.e. without a collet). The collet locking interface is preferred for its integrity in transmitting high loads and maintaining good alignment. A clamping interface is only need on the motor side, in order to transmit the motor torque.

Self-Alignment of Modular Lower Limb Device

In some example embodiments, the joint assembly may be adapted to include a joint alignment mechanism, in which anatomical reaction forces are employed to automatically adjust the length and rotation between two joint assemblies (z-alignment+rotation about z–where z is the direction along the axis of a connection rod connecting two adjacent joint assemblies).

Referring to FIG. 1A, once a modular lower limb device, formed from joint assemblies as described above, is fastened to the user through a cuff interface, thereby providing x & y alignment, the length degree of freedom between the joint assemblies (z-alignment) may be left unconstrained, such that the connection rods 130 and 135 are permitted to slide relative to the support frames of the joint assemblies.

Figure 12A:
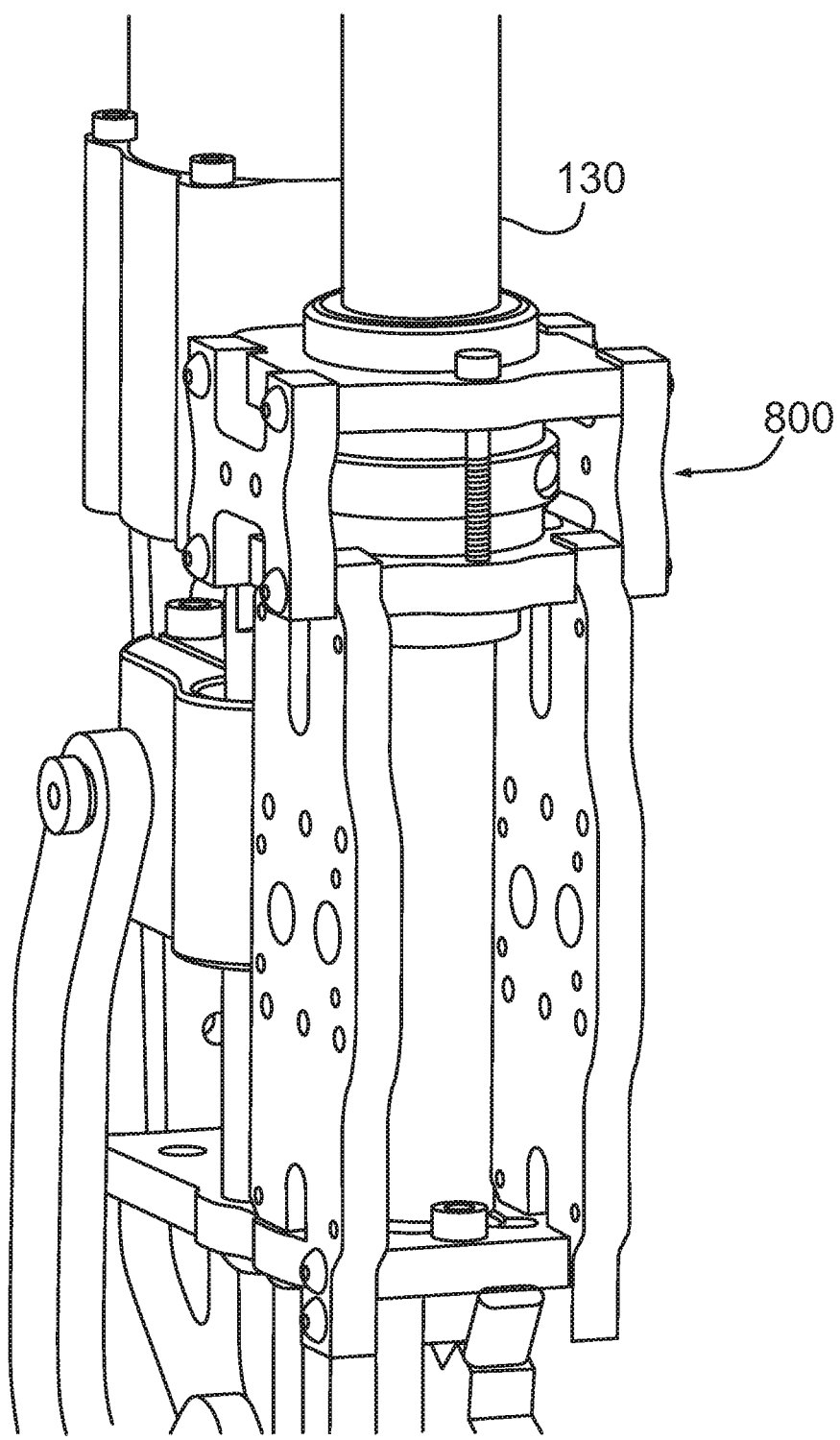
FIGS. 12A-B shows an example alignment system for aligning and adjusting the length of a connection rod between joint assemblies.
Figure 12B:
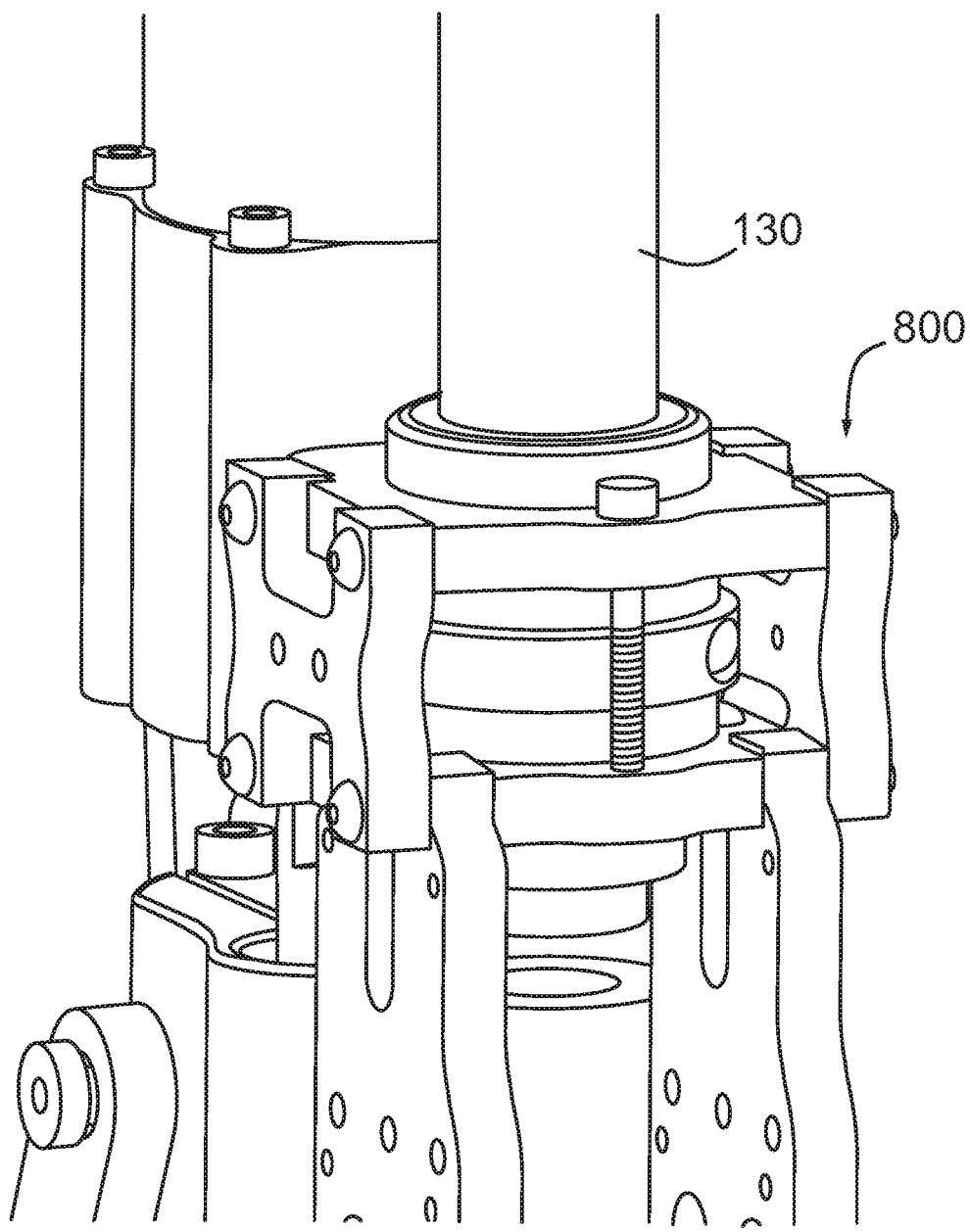

The relative slidable translation of a connection rod 130 relative to a given joint assembly 600 is illustrated in FIGS. 12A-B, where FIG. 12A shows the connection rod fully inserted into the support frame, through a locking assembly 800 (also shown in FIGS. 6A and 6B), in a configuration that minimizes the inter-joint separation. FIG. 12B shows the connection rod 130 in a configuration that maximizes the inter-joint separation. The user and device are then moved through some of the operating range of motion, and if any misalignment is present, the length of the connecting rod between the two joint assemblies will vary. If the x & y alignment from the cuff interface is correct, the rod will be coaxial to the anatomical joint axis, and the length between the joint assemblies will naturally converge to its anatomical neighbor. The length and rotation degree of freedom can then be locked; joint alignment is complete. If convergence does not happen and the joint length keeps varying throughout the range of motion, it would indicate that the x & y alignment is incorrect. In other example embodiments, alignment mechanism may also be provided to permit self-aligning capabilities also in the x and y directions.

Figure 13A:
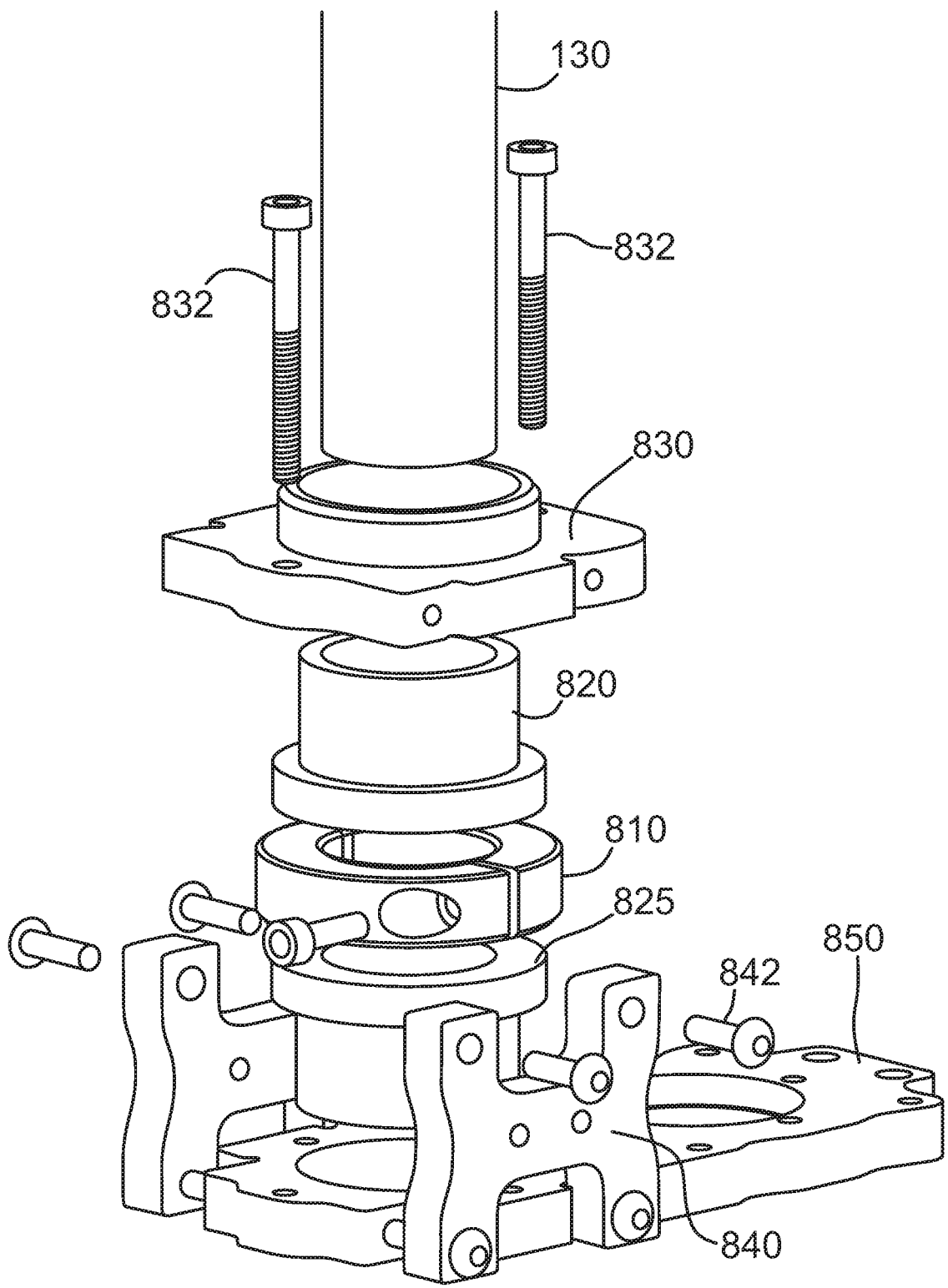
FIGS. 13A-B shows an assembly view of an example connection rod alignment system.
Figure 13B:
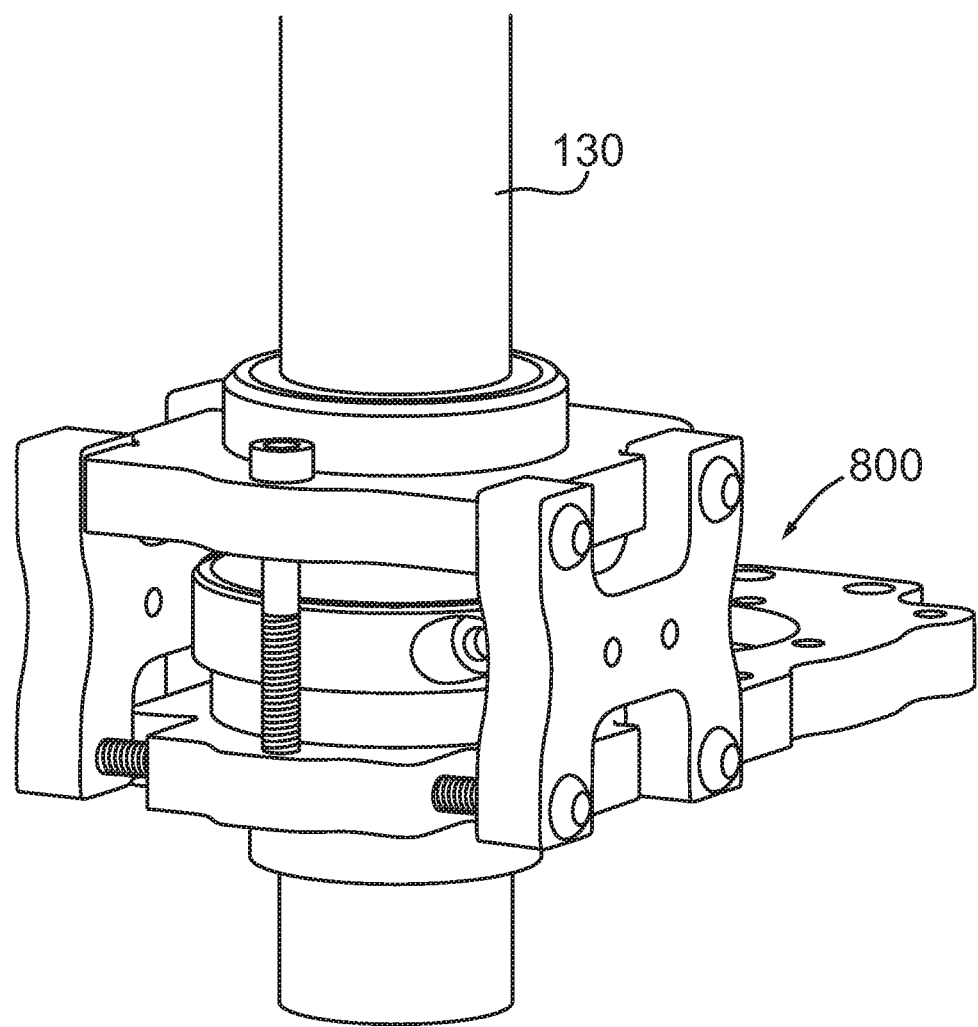
Figure 14:
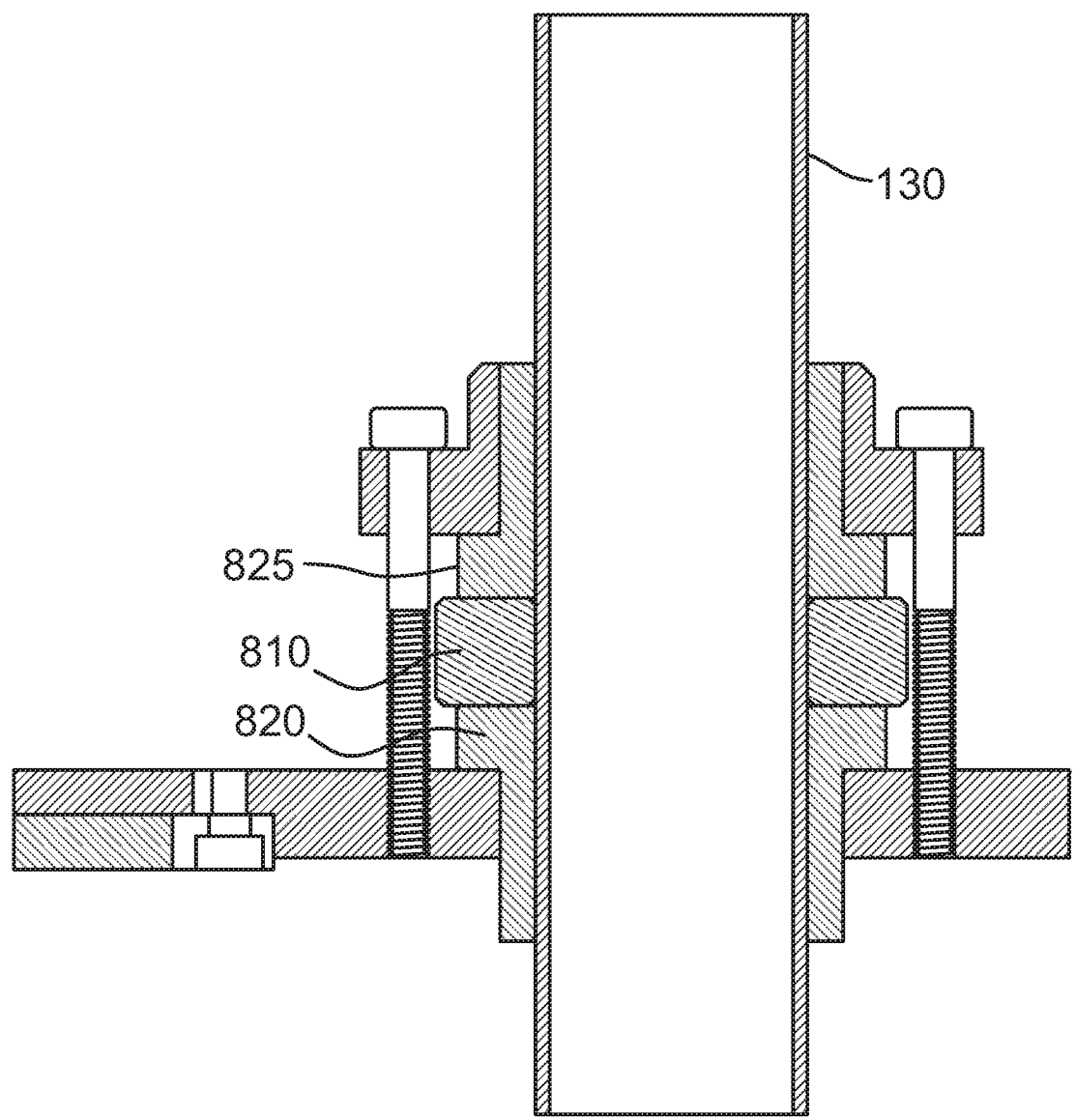
FIG. 14 shows a cross-sectional view of an example connection rod alignment system.

The locking of this degree of freedom (z) is realized by a clamping collar 810 that can be tightened to apply a clamping force around the connecting rod 130, as shown in FIGS. 13A-B and FIG. 14. Adjacent to both sides of the collar are two flanged bushings 820 and 825, which provide the sliding interface for the connecting rod 130. The flanges of the bushings 820, 825 provides a bearing surface against the collar if the rotation degree of freedom is desired to be kept free while the collar is locked (if the collar is unlocked, the length+rotation degrees of freedom will be free). To lock the rotation of the connecting rod 130, the two top screws 832 can be tightened to clamp both flanges of the bushings against the collar via pressure from the length adjustment top plate 830 and the linear shaft top plate 850. During tightening of the screws, the four screws 842 against length adjustment side plate 840 are kept loose. A slot in length adjustment side plate 840 allows for small vertical displacements of length adjustment top plate 830. This assures proper friction force between the collar 810 and flanged bushings 820, 825, and prevents unwanted rotation of the joint assembly.

In one example implementation, this connecting rod support within each joint assemblies is configured to permit a possible inter-joint length variation of 84 mm between the ankle and the knee (to account for differences in anatomical joint lengths), and 160 mm between the hip and the knee (two mechanisms with full range). This range is sufficient to accommodate a range of patients spanning a 1 percentile male to a 99th percentile male by variation of the separation between each joint.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A joint assembly for use with a modular powered prosthesis or a modular powered orthosis, the joint assembly comprising:
   a support frame;
   a motor supported by said support frame;
   a slider-crank mechanism comprising a crank and a coupling link, said crank being pivotally connected to said support frame, thereby forming a joint, wherein a distal portion of said coupling link is connectable to said crank at a plurality of selectable anchor points; and
   wherein each selectable anchor point is configured to provide a respective range of rotational travel, rotational speed, and torque that is customized for actuation of a different type of anatomical joint.

2. The joint assembly according to claim 1 further comprising a connection link means for receiving and securing a connection rod when connecting the joint assembly to an additional joint assembly to form the modular powered prosthesis or the modular powered orthosis.

3. The joint assembly according to claim 1 wherein said crank is pivotally mounted to said support frame at a location that is offset from a rotation axis of said motor.

4. The joint assembly according to claim 1 configured for use as a modular orthosis, the joint assembly further comprising a user mounting mechanism attached to said support frame for mounting the joint assembly to a limb of a user.

5. The joint assembly according to claim 1 wherein one of said selectable anchor points is an ankle joint anchor point for configuring the joint assembly to provide a torque and a range of rotational travel suitable for use as a powered ankle joint.

6. The joint assembly according to claim 5 wherein said ankle joint anchor point is selected such that the joint assembly is capable of providing a torque between 0.2 and 175 Nm, and a range of rotational travel within the range of 22.5 to 35 degrees.

7. The joint assembly according to claim 1 wherein one of said selectable anchor points is a knee joint anchor point for configuring the joint assembly to provide a torque and a range of rotational travel suitable for use as a powered knee joint.

8. The joint assembly according to claim 7 wherein said knee joint anchor point is selected such that the joint assembly is capable of providing a torque between 0.2 and 100 Nm, and a range of rotational travel within the range of 0 to 110 degrees.

9. The joint assembly according to claim 1 wherein one of said selectable anchor points is a hip joint anchor point for configuring the joint assembly to provide a torque and a range of rotational travel suitable for use as a powered hip joint.

10. The joint assembly according to claim 9 wherein said hip joint anchor point is selected such that the joint assembly is capable of providing a torque between 0.1 and 95 Nm, and a range of rotational travel within the range of 17.5 to 98 degrees.

11. The joint assembly according to claim 1 wherein said slider-crank mechanism comprises a screw coupled to an output shaft associated with said motor, said screw comprising a nut, and wherein said coupling link mechanically couples said nut to said crank, such that linear actuation of said nut by said motor responsively produces rotation of said crank about the joint, the joint assembly further comprising:
   at least one linear guide shaft fixed to said support frame such that each linear guide shaft is adjacent and parallel to said screw; and
   each linear guide shaft comprising a linear ball bearing; wherein each linear ball bearing of each linear guide shaft is mechanically coupled to said nut for guiding translation thereof.

12. The joint assembly according to claim 11 further comprising a guide member, wherein said nut is mechanically coupled to said guide member, and wherein each linear ball bearing is retained by said guide member such that linear motion of said nut is mechanically coupled to said each linear ball bearing through said guide member.

13. The joint assembly according to claim 12 wherein said coupling link is mechanically coupled to said nut through a connection with said guide member.

14. The joint assembly according to claim 1 wherein said slider-crank mechanism comprises a screw coupled to an output shaft associated with said motor, said screw comprising a nut, and wherein said coupling link mechanically couples said nut to said crank, such that linear actuation of said nut by said motor responsively produces rotation of said crank about the joint, the joint assembly further comprising a compact screw support assembly configured to connect said screw to said output shaft, said compact screw support assembly comprising:
- a coupling securing a screw shaft of said screw to said output shaft; and
- a coupling housing secured to a non-rotating portion of said motor;
- wherein said coupling is rotatably supported within said coupling housing by a first angular contact bearing and a second angular contact bearing; and
- wherein said first angular contact bearing and said second angular contact bearing are arranged in a back-to-back configuration and reside between an inner surface of said coupling housing and an outer surface of said coupling.

15. The joint assembly according to claim 14 wherein said coupling comprises:
- a main body having an inner bore, said main body comprising a proximal split clamp configured to clamp said output shaft within a proximal portion of said inner bore;
- a collet recessed within a distal tapered portion of said inner bore, wherein a distal portion of said screw is received within said collet; and
- a collet nut secured to a distal portion of said main body for securing said collet within said distal tapered portion of said inner bore, thereby locking said screw to said coupling.

16. The joint assembly according to claim 15 wherein an outer surface of said coupling comprises a proximal coupling shoulder, and wherein said first angular contact bearing and said second angular contact bearing are secured and preloaded relative to said coupling via contact with said proximal coupling shoulder and a distal lock nut retained on an outer surface of said coupling.

17. The joint assembly according to claim 16 wherein said proximal split clamp is clamped with a plurality of clamping bolts, and wherein said proximal split clamp comprises a plurality of counter bores for recessing respective heads of said clamping bolts and for use in preventing rotation of said coupling during tightening of said collet nut and said distal locking nut.

18. The joint assembly according to claim 15 wherein said coupling housing comprises a motor mounting portion and a distal housing portion, wherein said non-rotating portion of said motor is secured to said motor mounting portion, and wherein said motor mounting portion is secured to said distal housing portion to form said coupling housing, and wherein said motor mounting portion comprises a proximal housing shoulder and wherein said distal housing portion comprises distal housing shoulder, wherein outer portions of said first angular contact bearing and said second angular contact bearing are secured relative to said coupling housing via contact with said proximal housing shoulder and said distal housing shoulder.

19. The joint assembly according to claim 18 wherein said proximal housing shoulder comprises a plurality of apertures to permit insertion of clamping bolts within said proximal split clamp for clamping said proximal split clamp to said output shaft.

20. The joint assembly according to claim 15 wherein said collet is an ER collet.

21. The joint assembly according to claim 14 wherein said screw and said nut are components of a ball screw assembly.

22. The joint assembly according to claim 14 wherein said output shaft is a motor output shaft and a gearbox output shaft.

23. The joint assembly according to claim 1 wherein said coupling link is pivotally connected to said crank through a joint pin.

24. The joint assembly according to claim 23 wherein said joint pin is a double-d shaft.

25. A modular lower limb device comprising:
- an ankle joint assembly provided according to claim 1;
- a knee joint assembly provided according to claim 1; and
- a first connection rod connecting said ankle joint assembly to said knee joint assembly.

26. The modular lower limb device according to claim 25 further comprising:
- a hip joint assembly provided according to claim 10; and
- a second connection rod connecting said knee joint assembly to said hip joint assembly.

27. The modular lower limb device according to claim 25 wherein the modular lower limb device is a prosthetic device.

28. The modular lower limb device according to claim 25 wherein the modular lower limb device is an orthotic device.

* * * * *